(12) United States Patent
Schwab et al.

(10) Patent No.: US 9,340,535 B2
(45) Date of Patent: *May 17, 2016

(54) N-[5-(AMINOSULFONY1)-4-METHYL-1,3-THIAZOL-2-YL]-N-METHYL-2-[4-(2-PYRIDINYL)PHENYL]ACETAMIDE MESYLATE MONOHYDRATE

(71) Applicant: AiCuris GmbH & Co. KG, Wuppertal (DE)

(72) Inventors: Wilfried Schwab, Werder (DE); Alexander Birkmann, Wuppertal (DE); Kurt Vogtli, Oberhofen (CH); Dieter Haag, Ramlinsburg (CH); Andreas Lender, Wuppertal (DE); Alfons Grunenberg, Dormagen (DE); Birgit Keil, Dusseldorf (DE); Joachim Rehse, Leichlingen (DE)

(73) Assignee: AICURIS GMBH & CO. KG, Wuppertal (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/347,287

(22) PCT Filed: Sep. 26, 2012

(86) PCT No.: PCT/EP2012/068938
§ 371 (c)(1),
(2) Date: Mar. 26, 2014

(87) PCT Pub. No.: WO2013/045479
PCT Pub. Date: Apr. 4, 2013

(65) Prior Publication Data
US 2014/0221433 A1 Aug. 7, 2014

(30) Foreign Application Priority Data
Sep. 26, 2011 (EP) .................................. 11007823

(51) Int. Cl.
C07D 417/12 (2006.01)

(52) U.S. Cl.
CPC .................................. *C07D 417/12* (2013.01)

(58) Field of Classification Search
None
See application file for complete search history.

(56) References Cited

U.S. PATENT DOCUMENTS

| 7,105,553 B2 * | 9/2006 | Fischer et al. ................. 514/369 |
| 9,119,786 B2 * | 9/2015 | Schwab ............... C07D 417/12 |
| 2004/0006076 A1 | 1/2004 | Fischer et al. |
| 2008/0220059 A1 | 9/2008 | Laich et al. |

FOREIGN PATENT DOCUMENTS

| WO | 0147904 A1 | 7/2001 |
| WO | 2006103011 A1 | 10/2006 |

OTHER PUBLICATIONS

International Search Report for PCT/EP2012/068938 dated Nov. 26, 2012.
Betz, Ulrich A. K. et al, "Potent in vivo antiviral activity of the Herpes Simplex Virus Primase-Helicase Inhibitor BAY 57-1293," Antimicrobial Agents and Chemotherapy, Jun. 2002, vol. 46, No. 6, pp. 1766-1772.

\* cited by examiner

*Primary Examiner* — Timothy R Rozof
(74) *Attorney, Agent, or Firm* — Millen White Zelano and Branigan, PC; Csaba Henter; Anthony Zelano

(57) ABSTRACT

The present invention relates to an improved and shortened synthesis of N-[5-(aminosulfonyl)-4-methyl-1,3-thiazol-2-yl]-N-methyl-2-[4-(2-pyridinyl)phenyl]acet-amide and the mesylate monohydrate salt thereof by using boronic acid derivatives or borolane reagents while avoiding toxic organic tin compounds and to the mesylate monohydrate salt of N-[5-(aminosulfonyl)-4-methyl-1,3-thiazol-2-yl]-N-methyl-2-[4-(2-pyridinyl)phenyl]acet-amide which has demonstrated increased long term stability and release kinetics from pharmaceutical compositions.

25 Claims, 6 Drawing Sheets

Fig 1A

| | |
|---|---|
| formula | $C_{19}H_{24}N_4O_7S_3$ |
| formula weight | 516.62 |
| Z, calculated density | 2, 1.487 Mg·m$^{-3}$ |
| F(000) | 540 |
| description and size of crystal | colorless plate, 0.02 · 0.13 · 0.15 mm3 |
| absorption coefficient | 0.370 mm-1 |
| min/max transmission | 0.95/0.99 |
| temperature | 293K |
| radiation(wavelength) | Mo $K\alpha(\lambda = 0.71073$ Å) |
| Crystal system, space group | triclinic, P -1 |
| a | 9.4908(7) Å |
| b | 9.5545(7) Å |
| c | 14.4137(9) Å |
| α | 86.130(3)° |
| β | 72.104(3)° |
| γ | 68.253(4)° |
| V | 1153.68(15) Å$^3$ |
| min/max Θ | 2.426° / 30.065° |
| number of collected reflections | 43492 |
| number of independent refections | 6761 (merging r = 0.026) |
| number of observed reflections | 4955 (I>3.0σ(I)) |
| number of refined parameters | 298 |
| r | 0.0313 (observed data with ) |
| rW | 0.0432 (all data) |
| goodness of fit | 1.0736 |
| residual electron density | -0.28/0.33 e Å$^3$ |

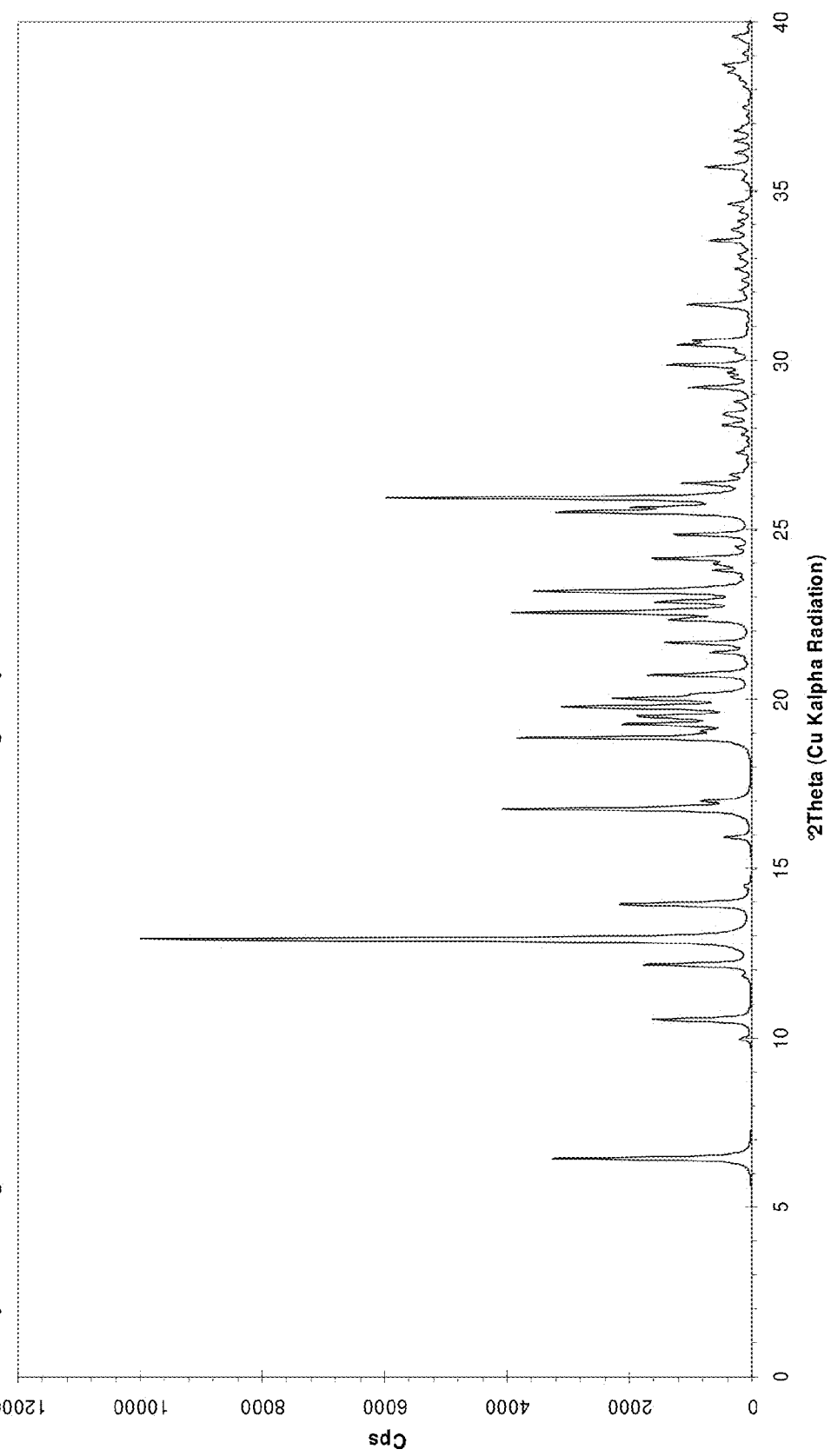

N-[5-(AMINOSULFONY1)-4-METHYL-1,3-THIAZOL-2-YL]-N-METHYL-2-[4-(2-PYRIDINYL)PHENYL]ACETAMIDE MESYLATE MONOHYDRATE

The present invention relates to an improved synthesis of N-[5-(aminosulfonyl)-4-methyl-1,3-thiazol-2-yl]-N-methyl-2-[4-(2-pyridinyl)phenyl]acetamide and the mesylate monohydrate salt thereof by using boronic acid derivatives or borolane reagents while avoiding toxic organic tin compounds and to the mesylate monohydrate salt of N-[5-(aminosulfonyl)-4-methyl-1,3-thiazol-2-yl]-N-methyl-2-[4-(2-pyridinyl)phenyl]acetamide which has demonstrated increased long term stability and release kinetics from pharmaceutical compositions.

BACKGROUND OF THE INVENTION

Synthesis of N-[5-(aminosulfonyl)-4-methyl-1,3-thiazol-2-yl]-N-methyl-2-[4-(2-pyridinyl)phenyl]acetamide is known from EP 1244641 B1, and the use of acidic components including methanesulfonic acid for the formulation of tablets containing micronized N-[5-(aminosulfonyl)-4-methyl-1,3-thiazol-2-yl]-N-methyl-2-[4-(2-pyridinyl)phenyl]acetamide is disclosed by WO 2006/103011 A1.

It is the objective of the present invention to provide an improved synthesis for the compound N-[5-(aminosulfonyl)-4-methyl-1,3-thiazol-2-yl]-N-methyl-2-[4-(2-pyridinyl)phenyl]acetamide and a stable salt which exhibits increased long term stability and improved release kinetics from pharmaceutical formulations as well as a pharmaceutical formulations comprising that salt with improved release kinetics.

The objective of the present invention is solved by the teaching of the independent claims. Further advantageous features, aspects and details of the invention are evident from the dependent claims, the description, the figures, and the examples of the present application.

DESCRIPTION OF THE INVENTION

The present invention relates to an improved and novel synthesis of the pharmaceutically active compound N-[5-(aminosulfonyl)-4-methyl-1,3-thiazol-2-yl]-N-methyl-2-[4-(2-pyridinyl)phenyl]acetamide as well as its mesylate salt. This improved synthesis starts from the same compounds as the older known synthesis of the state of the art but combines three reaction steps by the use of a boronic acid derivatives or borolane reagent. This modification makes the complete synthesis easier by avoiding two separation and purification steps and is also able to increase the yield.

The older known synthesis as described in EP 1244641 B1 on page 21 starts from 2-bromopyridine. In step 1 the 2-trimethylstannanylpyridine is prepared in a 45 to 50% yield (of the theory). The 2-trimethylstannanylpyridine is subsequently reacted with ethyl (4-bromophenyl)acetate in order to obtain the ethyl (4-pyridin-2-ylphenyl)acetate in a 75% yield. In the third step the ethyl (4-pyridin-2-ylphenyl)acetate is saponified to the (4-pyridin-2-ylphenyl)acetic acid with about 95% yield of theory. Consequently, the state of the art synthesis as shown below

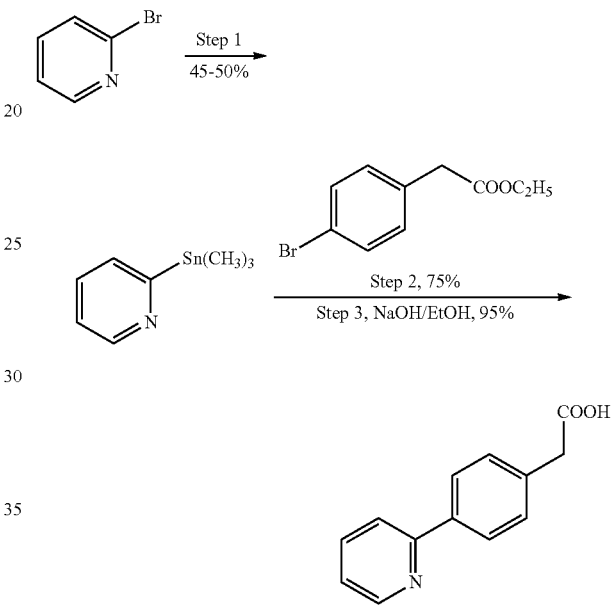

comprises 3 steps with an over all yield of about 34% including two separation and purification steps which take time and involve the use of solvents for extracting and washing the desired compounds as well as arrangements for purifying them.

The synthesis of the present invention as shown below

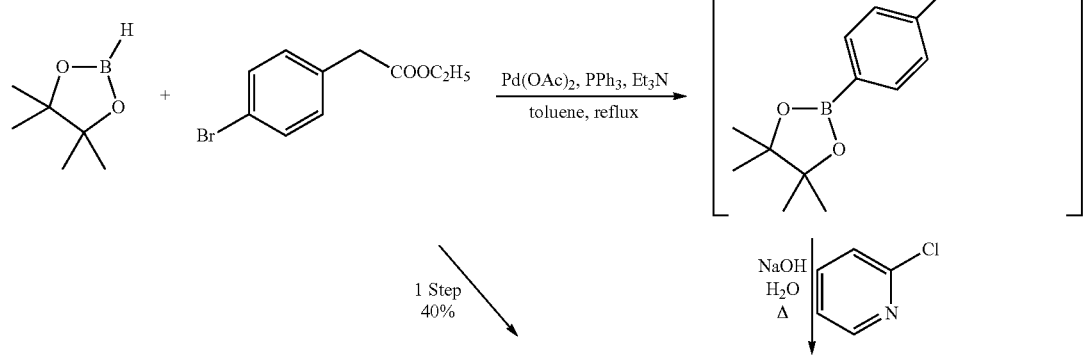

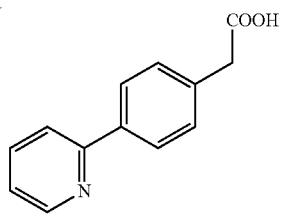

combines the three discrete steps by using boronic acid derivatives or borolane or a borinane reagent which allows for synthesis of the key intermediate (4-pyridin-2-ylphenyl)acetic acid in a single stage with an over all yield of about 40% of theory avoiding the two separation and purification steps of the state of the art synthesis.

As an added benefit, the use of boron containing reagents is advantageous over the use of the toxic organic tin compounds in that the resulting boric acid by-product can be easily removed by an aqueous wash. In contrast, organic tin compounds are not only a known problem in process waste streams, but are also noted for notoriously contaminating the resulting products of the down-stream synthesis. The (4-pyridin-2-ylphenyl)acetic acid is reacted with 4-methyl-2-(methylamino)-1,3-thiazole-5-sulfonamide to the final product which is then converted to the definite mesylate monohydrate salt as shown below.

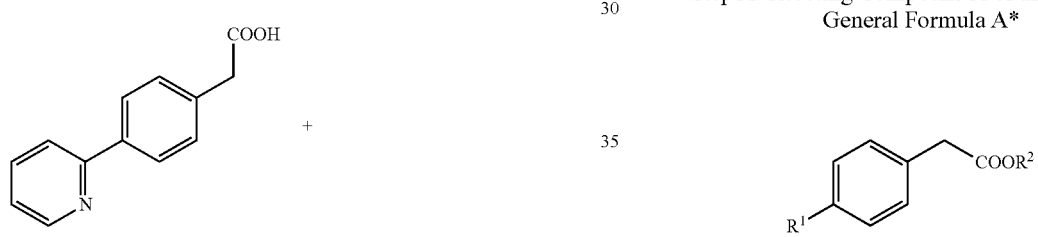

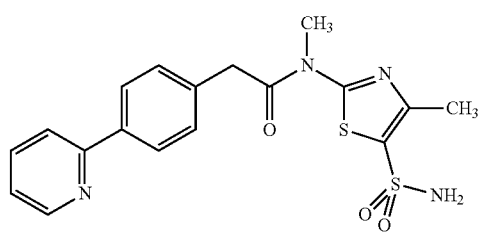

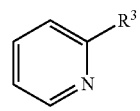

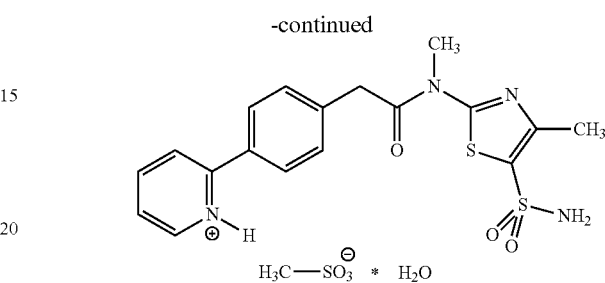

Thus the present invention is directed to a method for synthesizing N-[5-(aminosulfonyl)-4-methyl-1,3-thiazol-2-yl]-N-methyl-2-[4-(2-pyridinyl)phenyl]acetamide and the mesylate salt thereof according to the following steps:

Step A: Reacting Compound A of the Following General Formula A*

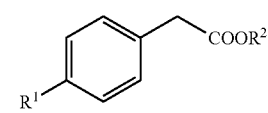

wherein
R$^1$ represents a leaving group and
R$^2$ represents an alkyl residue with 1 to 6 carbon atoms or a cycloalkyl residue with 3 to 6 carbon atoms,
with a boronic acid derivative, borolane, borinane or diboronic acid reagent under elimination of R$^1$—H or R$^1$—B(OR)$_2$ and formation of an intermediate boronic acid derivative of compound A,
wherein preferred catalysts for the reaction are the reagent systems palladium acetate with triethylamine and triphenylphosphine or PdCl$_2$(PPh$_3$)$_2$ with triethylamine,
wherein the intermediate boronic acid derivative is then reacted with the pyridine compound B of the following general formula B*

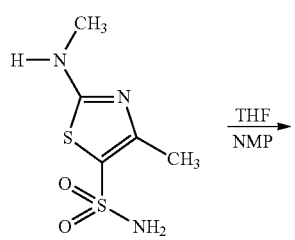

wherein
R$^3$ represents a leaving group
under basic conditions in order to obtain the (4-pyridin-2-ylphenyl)acetic acid as an alkaline solution of the corresponding carboxylate salt.

The resulting (4-pyridin-2-ylphenyl)acetic acid was purified by simple washings at different pH and clear filtration steps followed by precipitation or crystallization, preferably by properly adjusting the pH of an aqueous acidic solution of (4-pyridin-2-ylphenyl)acetic acid with an appropriate amount of base to 3.5-5.0, preferably 3.8-4.7. Beside the simple washing and filtration step, no further purification of the (4-pyridin-2-ylphenyl)acetic acid or any of the intermediates by, for instance, recrystallization or chromatography is required.

Step B: Reacting (4-pyridin-2-ylphenyl)acetic acid Obtained from Step A with 4-methyl-2-(methylamino)-1,3-thiazole-5-sulfonamide

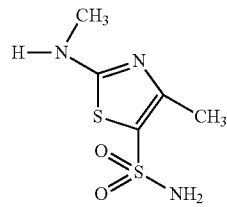

in order to obtain N-[5-(aminosulfonyl)-4-methyl-1,3-thiazol-2-yl]-N-methyl-2-[4-(2-pyridinyl)phenyl]acetamide of the formula

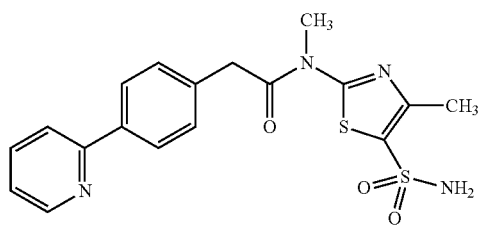 [SMILES: Cc1nc(N(C)C(=O)Cc2ccc(-c3ccccn3)cc2)sc1S(N)(=O)=O]

The N-[5-(aminosulfonyl)-4-methyl-1,3-thiazol-2-yl]-N-methyl-2-[4-(2-pyridinyl)-phenyl]acetamide is thereafter most preferably converted (as step C) to the so far unknown monohydrate of the mesylate salt of N-[5-(aminosulfonyl)-4-methyl-1,3-thiazol-2-yl]-N-methyl-2-[4-(2-pyridinyl)phenyl]acetamide. It has to be stated that a mesylate salt is disclosed in WO 2006/103011 A1 but not the specific mono mesylate monohydrate salt which exhibits the improved properties.

The inventive method for synthesizing the N-[5-(aminosulfonyl)-4-methyl-1,3-thiazol-2-yl]-N-methyl-2-[4-(2-pyridinyl)phenyl]-acetamide methanesulfonic acid mono-hydrate may further comprise step D directed to the preparation of a pharmaceutical composition of said methanesulfonic acid monohydrate salt:

Step D: Preparing a pharmaceutical composition of the crystalline N-[5-(aminosulfonyl)-4-methyl-1,3-thiazol-2-yl]-N-methyl-2-[4-(2-pyridinyl)phenyl]-acetamide methanesulfonic acid monohydrate with at least one pharmaceutically acceptable carrier, excipient, solvent and/or diluent Such a pharmaceutical composition can be prepared by admixing or blending the crystalline N-[5-(aminosulfonyl)-4-methyl-1,3-thiazol-2-yl]-N-methyl-2-[4-(2-pyridinyl) phenyl]-acetamide methanesulfonic acid monohydrate together with at least one pharmaceutically acceptable carrier, excipient, solvent and/or diluent.

The inventive method may further comprise step E following the step D:

Step E: Adding acetylsalicylic acid, trifluridine, idoxuridine, foscarnet, cidofovir, ganciclovir, aciclovir, penciclovir, valaciclovir and/or famciclovir to the pharmaceutical composition of the crystalline N-[5-(aminosulfonyl)-4-methyl-1,3-thiazol-2-yl]-N-methyl-2-[4-(2-pyridinyl)phenyl]-acetamide methanesulfonic acid monohydrate and at least one pharmaceutically acceptable carrier, excipient, solvent and/or diluent Thus after step E a pharmaceutical composition containing acetylsalicylic acid, trifluridine, idoxuridine, foscarnet, cidofovir, ganciclovir, aciclovir, penciclovir, valaciclovir or famciclovir or a pharmaceutical composition containing acetylsalicylic acid and trifluridine or acetylsalicylic acid and idoxuridine or acetylsalicylic acid and foscarnet or acetylsalicylic acid and cidofovir or acetylsalicylic acid and ganciclovir or acetylsalicylic acid and aciclovir or acetylsalicylic acid and penciclovir or acetylsalicylic acid and valaciclovir or acetylsalicylic acid and famciclovir in combination with crystalline N-[5-(aminosulfonyl)-4-methyl-1,3-thiazol-2-yl]-N-methyl-2-[4-(2-pyridinyl)phenyl]-acetamide methanesulfonic acid monohydrate together with at least one pharmaceutically acceptable carrier, excipient, solvent and/or diluent is obtained.

Consequently the present invention relates also to a pharmaceutical composition containing acetylsalicylic acid or aciclovir or penciclovir or acetylsalicylic acid and aciclovir or acetylsalicylic acid and penciclovir and crystalline N-[5-(aminosulfonyl)-4-methyl-1,3-thiazol-2-yl]-N-methyl-2-[4-(2-pyridinyl)phenyl]-acetamide methanesulfonic acid monohydrate together with at least one pharmaceutically acceptable carrier, excipient, solvent and/or diluent. Some suppliers use the name acyclovir instead of aciclovir.

The term "leaving group" as used herein is a molecular fragment that departs with a pair of electrons in heterolytic bond cleavage. Leaving groups can be anions or neutral molecules. Common anionic leaving groups are halides such as Cl$^-$, Br$^-$, and I$^-$, and sulfonate esters, such as para-toluenesulfonate ("tosylate", TsO$^-$), trifluoromethanesulfonate ("triflate", TfO$^-$, CF$_3$SO$_2$O$^-$), benzenesulfonate ("besylate, C$_6$H$_5$SO$_2$O$^-$) or methanesulfonate ("mesylate", MsO$^-$).

General formula A* as shown below

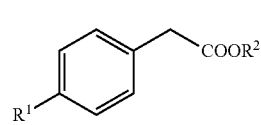

covers all phenyl acetic acid esters having a leaving group on the phenyl residue in position 4.

Thus R$^1$ preferably represents —F, —Cl, —Br, —I, —OMs, —OTf and —OTs. The group "—OMs" refers to —OMesylate, the group "—OTf" refers to —OTriflate and the group "—OTs" refers to —OTosylate.

The group R$^2$ represents an alkyl residue with 1 to 6 carbon atoms or a cycloalkyl residue with 3 to 6 carbon atoms, and preferably —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C₅H₁₁, —C₆H₁₃, cyclo-C₃H₅, cyclo-C₄H₇, cyclo-C₅H₉, cyclo-C₆H₁₁. More preferred are —CH₃, —C₂H₅, —C₃H₇, —CH(CH₃)₂, —C₄H₉, —CH₂—CH(CH₃)₂, —CH(CH₃)—C₂H₅, —C(CH₃)₃, and —C₅H₁₁. Especially preferred are —CH₃, —C₂H₅, —C₃H₇, and —CH(CH₃)₂.

Various borolanes and borinanes as well as the corresponding diboronic acid derivatives can be used in step A of the inventive synthesis disclosed herein. Preferred are borolanes of the following general formula:

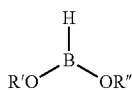

wherein
R' and R" are independently of each other any substituted or unsubstituted, linear or branched alkyl group with 1 to 10 carbon atoms or cycloalkyl group with 3 to 10 carbon atoms, or R' and R" can also form together with the boron atom a heterocyclic ring wherein R' and R" together form a substituted or unsubstituted, linear or branched alkylen group with 2 to 10 carbon atoms. Preferably R' and R" represent independently of each other —CH₃, —C₂H₅, —C₃H₇, —CH(CH₃)₂, —C₄H₉, —CH₂—CH(CH₃)₂, —CH(CH₃)—C₂H₅, —C(CH₃)₃, and —C₅H₁₁. The cyclic borolanes are preferred.

The following borolanes, borinanes and diboronic acid derivatives are preferred:

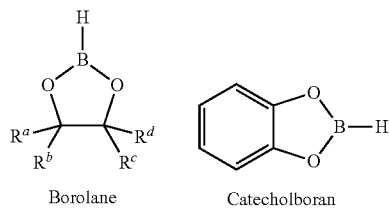

Borolane    Catecholboran

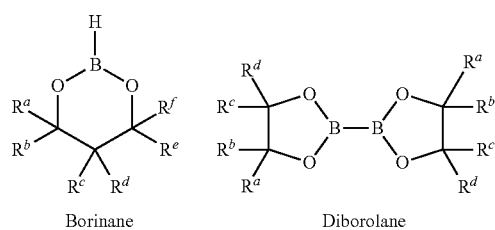

Borinane    Diborolane

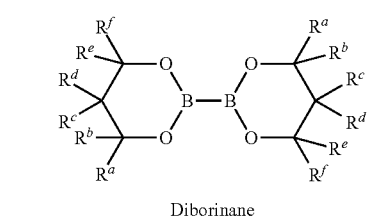

Diborinane wherein $R^a$, $R^b$, $R^c$, $R^d$, $R^e$ and $R^f$ represent independently of each other a substituted or unsubstituted, linear or branched alkyl group with 1 to 10 carbon atoms or cycloalkyl group with 3 to 10 carbon atoms. Preferred are the linear alkyl residues with 1 to 6 carbon atoms, and most preferred are —CH₃, —C₂H₅, —C₃H₇ and —CH(CH₃)₂.

Especially preferred examples for the above borone containing compounds are 4,4,5,5-tetramethyl[1,3,2]dioxaborolane (pinacolborane), [1,3,2]dioxaborolane, [1,3,2]dioxaborinane, 5,5-dimethyl[1,3,2]dioxaborinane, 4,6,6-trimethyl[1,3,2]-dioxaborinane, 4,4,6,6-tetramethyl[1,3,2]-dioxaborinane, 4,4,5,5,6,6-hexamethyl[1,3,2]-dioxaborinane, diisopropoxyborane, hexahydrobenzo[1,3,2]di-oxaborole, 9,9-dimethyl-3,5-dioxa-4-bora-tricyclo-[6.1.1.6$^{2,6}$]decane, 6,9,9-trimethyl-3,5-dioxa-4-bora-tricyclo[6.1.1.6$^{2,6}$]decane, B₂Pin₂ (bis(pinacolato)diborane), bis(neopentylglycolato)diboron and catecholboran.

In step A this boronic acid derivative, borolane, borinane or diboronic acid reagent is reacted with a compound A of general formula A* in order to obtain an intermediate borolan or borinane reagent which is not isolated and purified. This reaction may be supported by the use of either catalysts prepared in situ by combination of palladium salts such as [Pd(OAc)₂] and PdCl₂ with triphenylphosphine (PPh₃), tri-ortho-tolylphosphine (P(o-Tol)₃), tricyclohexylphosphine (PCy₃), tri-tert.-butylphosphine, 1,4-Bis-(diphenylphosphino)-butane (dppb), and 1,1'-Bis-(diphenylphosphino)-ferrocene dppf or preformed catalysts such as Pd(PPh₃)₂Cl₂, Pd(PPh₃)₄, Fibrecat 1032, and Pd(dppf)Cl₂ in the presence of a variety of organic and inorganic bases such as triethylamine (Et₃N), NaOAc, KOAc, and K₃PO₄. For this reaction heating to temperature between 70° C. and 150° C., preferably between 80° C. and 130° C., more preferably between 90° C. and 110° C. is preferred. Moreover aprotic and preferably apolar solvents and preferably aromatic solvents such as benzene or toluene or xylenes are used.

This step A improves the state of the art synthesis by avoiding the use of toxic organic tin compounds which are a big problem in the purification of the waste streams as well as the actual product(s) of the reaction which are finally drugs for use in humans.

The intermediate boronic acid reagent is subsequently reacted with a pyridinyl compound of the general formula B*, wherein $R^3$ represents a leaving group. Thus $R^3$ represents —F, —Cl, —Br, —I, —OMs, —OTf and —OTs and preferably —Cl or —Br. The corresponding (4-pyridin-2-ylphenyl) acetic acid ester is in situ treated with an aqueous base in order to cleave the ester linkage. It could be advantageous to heat the reaction mixture during the coupling/saponification step to moderate temperature and preferably to temperature between 40° C. and 90° C., more preferably between 45° C. and 80° C., still more preferably between 50° C. and 70° C. and most preferably between 55° C. and 65° C.

After purification and isolation of the key intermediate (4-pyridin-2-ylphenyl)acetic acid, the (4-pyridin-2-ylphenyl) acetic acid was obtained in a yield of at least 40% of theory including only one isolation and purification step.

Further advantages of the present method are:
Purification and Pd removal by successive washes of aqueous alkaline and acidic product solutions with organic solvents (toluene, MIBK, EtOAc, MeTHF etc.).
Additional Pd depletion by charcoal/Celite treatment.
Crystallization is possible from either alkaline or acidic aqueous solutions by neutralization (at preferably 50-70° C.)

Thereafter the (4-pyridin-2-ylphenyl)acetic acid was reacted with 4-methyl-2-(methylamino)-1,3-thiazole-5-sulfonamide of the formula

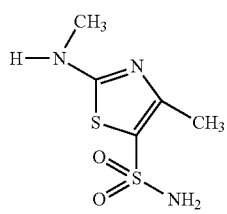

which was prepared according to the synthesis disclosed in EP 1244641 B1 in order to obtain N-[5-(aminosulfonyl)-4-methyl-1,3-thiazol-2-yl]-N-methyl-2-[4-(2-pyridinyl)phenyl]acetamide of the formula

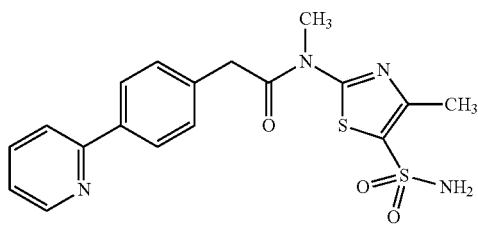 [SMILES: Cc1nc(N(C)C(=O)Cc2ccc(-c3ccccn3)cc2)sc1S(N)(=O)=O]

In WO 01/47904 A the amide coupling reaction is described using HOBT (1-Hydroxy-1H-benzotriazole hydrate) in DMF which—due to its explosive character—generally causes problems during up-scaling. In addition, during the optimization process the solvent DMF had been detected as cause for a variety of by-products (from Vilsmaier type formylations).

Attempts for improved coupling conditions resulted surprisingly in the successful use of EDCxHCl (1-ethyl-3-(3-dimethylaminopropyl)carbodiimide hydrochloride) without HOBT in NMP/THF solvent combinations. Thus Step B of the above-mentioned method is preferably carried out with EDCxHCl as coupling agent (without HOBT) in THF/NMP solvent mixtures having a ratio of 10:1 to 1:1. The following re-crystallization from THF/water resulted in a depletion of Pd to <5 ppm. A total yield of >80% for coupling and recrystallization could be achieved.

Thus the present invention also relates to the compound N-[5-(aminosulfonyl)-4-methyl-1,3-thiazol-2-yl]-N-methyl-2-[4-(2-pyridinyl)phenyl]acetamide obtained according to the synthesis as disclosed herein.

This N-[5-(aminosulfonyl)-4-methyl-1,3-thiazol-2-yl]-N-methyl-2-[4-(2-pyridinyl)-phenyl]acetamide was thereafter converted to the crystalline mesylate monohydrate salt which was not disclosed in the state of the art so far. A not stoichiometric mesylate salt was already known in the state of the art, but not the definite and stoichiometric mono mesylate monohydrate salt having exactly one mol equivalent water and one mol equivalent mesylate per mol equivalent N-[5-(aminosulfonyl)-4-methyl-1,3-thiazol-2-yl]-N-methyl-2-[4-(2-pyridinyl)-phenyl]acetamide.

Thus the present invention relates to the compound N-[5-(aminosulfonyl)-4-methyl-1,3-thiazol-2-yl]-N-methyl-2-[4-(2-pyridinyl)-phenyl]acetamide methanesulfonic acid monohydrate and especially to crystalline N-[5-(aminosulfonyl)-4-methyl-1,3-thiazol-2-yl]-N-methyl-2-[4-(2-pyridinyl)-phenyl]acetamide methanesulfonic acid mono-hydrate as well as to crystalline N-[5-(aminosulfonyl)-4-methyl-1,3-thiazol-2-yl]-N-methyl-2-[4-(2-pyridinyl)-phenyl]acetamide methanesulfonic acid monohydrate obtainable and obtained according to the synthesis as disclosed herein. The N-[5-(aminosulfonyl)-4-methyl-1,3-thiazol-2-yl]-N-methyl-2-[4-(2-pyridinyl)-phenyl]acet-amide methanesulfonic acid monohydrate is substantially pure (purity above 96 weight-%, preferably >98 weight-% and more preferably >99 weight-%) and is the definite monohydrate, i.e. 1 mol N-[5-(aminosulfonyl)-4-methyl-1,3-thiazol-2-yl]-N-methyl-2-[4-(2-pyridinyl)-phenyl]acetamide methanesulfonic acid monohydrate contains 1 mol water and 1 mol mesylate anion in a regular crystalline structure as shown in FIGS. 2 and 3.

The crystalline mesylate monohydrate salt of N-[5-(aminosulfonyl)-4-methyl-1,3-thiazol-2-yl]-N-methyl-2-[4-(2-pyridinyl)-phenyl]acetamide is formed from a supersaturated solution of N-[5-(aminosulfonyl)-4-methyl-1,3-thiazol-2-yl]-N-methyl-2-[4-(2-pyridinyl)-phenyl]acetamide and methanesulfonic acid by crystallization under controlled conditions. Preferred conditions for the crystallization are the addition of methanesulfonic acid at elevated temperatures, and preferably between 30° C. and 90° C., more preferably between 35° C. and 80° C., still more preferably between 40° C. and 70° C., still more preferably between 45° C. and 60° C. and most preferably at 50° C.-55° C. to the mixture of an organic solvent and water containing N-[5-(aminosulfonyl)-4-methyl-1,3-thiazol-2-yl]-N-methyl-2-[4-(2-pyridinyl)phenyl]acet-amide yielding a supersaturated solution of the mesylate of N-[5-(aminosulfonyl)-4-methyl-1,3-thiazol-2-yl]-N-methyl-2-[4-(2-pyridinyl)phenyl]acetamide. Organic solvents which are miscible or consolute with water are preferred such as MeOH, EtOH, n-PrOH, I—PrOH, acetonitrile, THF, acetone. Moreover it is preferred to add seed crystals of N-[5-(aminosulfonyl)-4-methyl-1,3-thiazol-2-yl]-N-methyl-2-[4-(2-pyridinyl)phenyl]acetamide methanesulfonic acid monohydrate to this supersaturated mixture also at elevated temperatures like 30° C. to 90° C., preferably 35° C. to 80° C., more preferably 40° C. to 70° C., still more preferably 45° C. to 60° C. and most preferably at 50° C.-55° C. Also moderate to slow stirring of this mixture and a slow cooling of this mixture to room temperature are preferred. Furthermore it is preferred to add the methanesulfonic acid over 5 to 15 minutes at the elevated temperature and to keep the resulting mixture at this elevated temperature for 0.5 to 5 hour and more preferably 1 to 2 hours after completion of the addition of the methanesulfonic acid. The cooling to room temperature is performed within 1 to 5 hour and preferably 2 to 3 hours and the mixture is thereafter slowly stirred for preferably another hour at room temperature. Then the crystals are filtered off, washed with alcohol/water and preferably dried under vacuum at a temperature between 20° C. and 60° C., preferably starting at 20° C. and ending at 60° C.

The crystalline mesylate monohydrate salt of N-[5-(aminosulfonyl)-4-methyl-1,3-thiazol-2-yl]-N-methyl-2-[4-(2-pyridinyl)phenyl]acetamide exhibits increased long term stability properties and a desired or improved release kinetic especially from pharmaceutical compositions and thus allows the preparation of long term stable pharmaceutical compositions. The long term stability of the crystalline mono mesylate monohydrate salt of N-[5-(aminosulfonyl)-4-methyl-1,3-thiazol-2-yl]-N-methyl-2-[4-(2-pyridinyl)phenyl]acetamide is superior in comparison to the free base form of N-[5-(aminosulfonyl)-4-methyl-1,3-thiazol-2-yl]-N-methyl-2-[4-(2-pyridinyl)phenyl].

Moreover the crystalline mono mesylate monohydrate salt of N-[5-(aminosulfonyl)-4-methyl-1,3-thiazol-2-yl]-N-methyl-2-[4-(2-pyridinyl)phenyl]acetamide exhibits also polymorphic stability in comparison to the free base form or other salts as evident from Table 1. Polymorphism refers to the ability of a solid material to exist in more than one crystal structure or solid form.

TABLE 1

Thermal analysis and polymorphic stability
(Methods used: DSC, TGA)

| Form | TGA | Thermal stability of hydrate | DSC |
|---|---|---|---|
| 1×HCl | 2.1% | labile | loss of water before melting |
| 1×MsOH | 4.3% | stable | loss of water before melting |
| 1×TsOH | 5.9% | labile | loss of water before melting |
| Free Base | 8.8% | labile | loss of water before melting |

TGA: Thermogravimetric Analysis or Thermal Gravimetric Analysis
DSC: Differential Scanning Calorimetry
Form: refers to the mono chloride salt, the mono mesylate salt, the mono tosylate salt and the free base of N-[5-(aminosulfonyl)-4-methyl-1,3-thiazol-2-yl]-N-methyl-2-[4-(2-pyridinyl)phenyl]acetamide The free base form as well as the hydrochloride and tosylate salts form hydrates of low thermal and low polymorphic stability. Upon mild heating (about 50° C. to 60° C.), the water content is reduced which would make these salts and the free base form extremely difficult to handle and to process during production and formulation. In contrast the hydrate of the mono mesylate salt is thermally stable and polymorphic stable at much higher temperatures of considerably above 100° C. as judged by TGA.

The free base of N-[5-(aminosulfonyl)-4-methyl-1,3-thiazol-2-yl]-N-methyl-2-[4-(2-pyridinyl)-phenyl]acetamide exists in four polymorphic forms and an amorphous form at room temperature. In addition, several solvates can be detected for the free base depending on the solvent. The data currently available do not permit the identification of the thermodynamically most stable form because all batches synthesised according to prior art display more than one melting peak by differential scanning calorimetry. The physicochemical properties of various salts (hydrochloride HCl, mesylate MsOH, tosylate TsOH) as well as of the free base have been investigated and compared (see Table 2).

methyl-2-[4-(2-pyridinyl)-phenyl]acetamide do not meet the criterion of stoichiometry. In addition, the hydrate of the monohydrochloride salt shows a decrease of crystallinity during storage. Furthermore, the free base and the monotosylate form hydrates with low thermal stability making them unsuitable for tabletting. These results are disclosed in Table 1 above, where the polymorphic instability of the hydrochloride salt, the tosylate salt and the free base form are discussed. Thus surprisingly only the inventive mono mesylate salt exhibited the required polymorphic and thermal stability in order to allow manufacture, processing and formulation especially in a pharmaceutical scale.

One possibility to prepare the crystalline N-[5-(aminosulfonyl)-4-methyl-1,3-thiazol-2-yl]-N-methyl-2-[4-(2-pyridinyl)-phenyl]acetamide methanesulfonic acid monohydrate was by dissolving the base in 10 vol ethanol/water (1:1), adding 1.15 equivalents of methanesulfonic acid at 50-55° C. during 5-15 min, seeding with 0.5 mol % of final product, ageing for 1-1.5 h at 50° C. and cooling to 20-25° C. during 2.5 h. After further stirring for 1 h, the crystalline mesylate monohydrate was isolated by filtration and dried in vacuo, resulting in a yield of >95%. Using this procedure, N-[5-(aminosulfonyl)-4-methyl-1,3-thiazol-2-yl]-N-methyl-2-[4-(2-pyridinyl)-phenyl]acet-amide methanesulfonic acid monohydrate in purity >99% containing <2 ppm residual Pd could be prepared reproducibly concerning yield and purity.

Further, the crystalline N-[5-(aminosulfonyl)-4-methyl-1,3-thiazol-2-yl]-N-methyl-2-[4-(2-pyridinyl)-phenyl]acetamide methanesulfonic acid monohydrate can be prepared in a defined and stable polymorphic form and in addition the co-precipitation of the less soluble free base form is avoided applying this process. Consequently the crystalline mesylate monohydrate of the present invention is free or substantially free of free base.

The inventive crystalline mesylate monohydrate salt further shows stability (as pure API and in pharmaceutical for-

TABLE 2

Salt screening for N-[5-(aminosulfonyl)-4-methyl-1,3-thiazol-2-yl]-N-methyl-2-[4-(2-pyridinyl)-phenyl]acetamide.

| Property | 1x HCl | 2x HCl | 1x MsOH | 2x MsOH | 1x TsOH | 2x TsOH | 1x PhCOOH | Free base | Determined by |
|---|---|---|---|---|---|---|---|---|---|
| Final processing | + | + | + | + | + | + | + | + | Preparation and crystallisation |
| Stability to dissociation | ++ | -- | ++ | -- | ++ | -- | -- | n.a. | Stirring for one week at room temperature |
| Purity | + | -- | + | -- | + | -- | -- | + | HPLC: ≥98%, correct stoichiometry |
| Crystallinity | -- | n.d. | + | n.d | + | n.d | n.d | + | X-ray diffraction, microscopy |
| Water solubility (mg/100 mL) | 39.4 | n.d | 138.3 | n.d | 50 | n.d | n.d | 0.2 | Solubility screening |
| Stability to decomposition | ++ | n.d. | ++ | n.d | – | n.d | n.d | ++ | Storage at 90° C. for one week | n.a. not applicable,
n.d. not determined,
HPLC high pressure liquid chromatography, ++ very good/high + good/high, – bad/low, -- very bad/low.

Dihydrochloride (2×HCl), dimesylate (2×MsOH), ditosylate (2×TsOH) and benzoate (1×PhCOOH) salts of the free base of N-[5-(aminosulfonyl)-4-methyl-1,3-thiazol-2-yl]-N-methyl-2-[4-(2-pyridinyl)-phenyl]acetamide do not meet the mulations) in long term stability studies, exhibits increased release kinetics from pharmaceutical compositions and leads to improved bioavailability.

As evident from FIG. 2 which shows the single-crystal X-ray structure analysis of the N-[5-(aminosulfonyl)-4-methyl-1,3-thiazol-2-yl]-N-methyl-2-[4-(2-pyridinyl)phenyl]-acetamide methanesulfonic acid monohydrate, the salt is formed between the mesylate and the protonated pyridinyl ring. Moreover, exactly one mol equivalent water is incorporated into the crystal structure wherein the hydrogen atoms of the water molecule form hydrogen bridges with oxygen atoms of two different mesylate molecules. This well-defined position in the crystal lattice (see FIG. 3) is verified by the fact that water is released from the crystal only at high temperature, starting at 160° C. Thus the inventive compound is a definite mono mesylate and mono hydrtate of N-[5-(aminosulfonyl)-4-methyl-1,3-thiazol-2-yl]-N-methyl-2-[4-(2-pyridinyl)-phenyl]-acetamide.

The crystalline N-[5-(aminosulfonyl)-4-methyl-1,3-thiazol-2-yl]-N-methyl-2-[4-(2-pyridinyl)-phenyl]acetamide methanesulfonic acid monohydrate according to the invention is a useful compound for the preparation of a pharmaceutical composition for treatment and/or prophylaxis of herpes virus infections and/or prevention of transmission of a herpes virus or herpes viruses. Pharmacokinetic data derived from single and multiple dose applications in healthy volunteers exhibited favourable plasma concentration over time profiles with long lasting half lives indicative for an once daily dosing regimen or less frequent such as once weekly. The plasma concentrations in humans exceeded those reached in in vivo and in vitro experiments sufficient to effectively treat herpes simplex virus infections in various animal models and to prevent viral replication in cell culture.

Surprisingly it was found that crystalline N-[5-(aminosulfonyl)-4-methyl-1,3-thiazol-2-yl]-N-methyl-2-[4-(2-pyridinyl)-phenyl]acetamide methanesulfonic acid monohydrate is highly active against herpes viruses and infections caused by herpes viruses, mainly herpes simplex viruses. Therefore the inventive crystalline N-[5-(aminosulfonyl)-4-methyl-1,3-thiazol-2-yl]-N-methyl-2-[4-(2-pyridinyl)-phenyl]acetamide methanesulfonic acid monohydrate is especially useful for the treatment and/or prophylaxis of diseases, which are caused by herpes simplex viruses, and/or prevention of transmission of a herpes virus or herpes viruses.

Infections with herpes simplex viruses (HSV, subtype 1 and 2) are categorized into one of several distinct disorders based on the site of infection. Orofacial herpes virus infection, the visible symptoms of which are colloquially called cold sores or fever blisters, infects the face and mouth. Orofacial herpes is the most common form of infection. Genital herpes is the second common form of a herpes simplex virus infection. Although genital herpes is largely believed to be caused by HSV-2 only, genital HSV-1 infections are increasing. Other disorders such as herpetic whitlow, herpes gladiatorum, ocular herpes (keratitis), cerebral herpes infection encephalitis, Mollaret's meningitis, neonatal herpes, and possibly Bell's palsy are also caused by herpes simplex viruses.

Further, the present invention relates to crystalline N-[5-(aminosulfonyl)-4-methyl-1,3-thiazol-2-yl]-N-methyl-2-[4-(2-pyridinyl)-phenyl]acetamide methanesulfonic acid monohydrate in combination with an anti-inflammatory agent. Especially preferred is a combination of crystalline N-[5-(aminosulfonyl)-4-methyl-1,3-thiazol-2-yl]-N-methyl-2-[4-(2-pyridinyl)-phenyl]acetamide methanesulfonic acid monohydrate and acetylsalicylic acid.

Furthermore, the present invention relates to crystalline N-[5-(aminosulfonyl)-4-methyl-1,3-thiazol-2-yl]-N-methyl-2-[4-(2-pyridinyl)-phenyl]acetamide methane-sulfonic acid monohydrate in combination with an anti-viral agent. The further anti-viral agent is preferably an antimetabolite and most preferably a nucleobase analogues, nucleotide analogues or nucleoside analogue drug. It is further preferred if the further anti-viral agent is useful against herpes viruses and/or against transmission of a herpes virus or herpes viruses and is selected from the group of drugs comprising but not limited to or consisting of: trifluridine, idoxuridine, foscarnet, cidofovir, ganciclovir, aciclovir or penciclovir or the respective prodrugs valaciclovir or famciclovir. Most preferred is a combination of crystalline N-[5-(aminosulfonyl)-4-methyl-1,3-thiazol-2-yl]-N-methyl-2-[4-(2-pyridinyl)-phenyl]-acetamide methanesulfonic acid monohydrate and aciclovir or penciclovir or the respective prodrugs valaciclovir and famciclovir.

The combination of crystalline N-[5-(aminosulfonyl)-4-methyl-1,3-thiazol-2-yl]-N-methyl-2-[4-(2-pyridinyl)-phenyl]acetamide methanesulfonic acid monohydrate and a further active agent (like anti-inflammatory, immunomodulatory, or anti-viral agents, e.g. therapeutic vaccines, siRNAs, antisense oligonucleotides, nanoparticles or virus uptake inhibitors such as n-docosanol) may be administered simultaneously in one single pharmaceutical composition or in more than one pharmaceutical composition, wherein each composition comprises at least one active agent.

The inventive compound is preferably used for the production of a pharmaceutical composition containing crystalline N-[5-(aminosulfonyl)-4-methyl-1,3-thiazol-2-yl]-N-methyl-2-[4-(2-pyridinyl)phenyl]acetamide methanesulfonic acid monohydrate together with at least one pharmaceutically acceptable carrier, excipient, solvent and/or diluent. The crystalline N-[5-(aminosulfonyl)-4-methyl-1,3-thiazol-2-yl]-N-methyl-2-[4-(2-pyridinyl)phenyl]acetamide methanesulfonic acid monohydrate used is free or substantially free of the free base form of N-[5-(aminosulfonyl)-4-methyl-1,3-thiazol-2-yl]-N-methyl-2-[4-(2-pyridinyl)phenyl]acetamide.

The pharmaceutical compositions of the present invention can be prepared in a conventional solid or liquid carrier or diluents and a conventional pharmaceutically-made adjuvant at suitable dosage level in a known way. Preferred preparations may be adapted for oral application. These administration forms include, for example, pills, tablets, film tablets, coated tablets, capsules, liposomal formulations, micro- and nano-formulations, powders and deposits.

The pharmaceutical compositions according to the invention preferably comprises 5 to 70% more preferably 10 to 30% by weight crystalline N-[5-(aminosulfonyl)-4-methyl-1,3-thiazol-2-yl]-N-methyl-2-[4-(2-pyridinyl)-phenyl]acetamide methane-sulfonic acid monohydrate (all percentage data are percentages by weight based on the weight of the pharmaceutical preparations). The pharmaceutical composition comprises usually 2 to 600 mg of crystalline N-[5-(aminosulfonyl)-4-methyl-1,3-thiazol-2-yl]-N-methyl-2-[4-(2-pyridinyl)-phenyl]acetamide methane-sulfonic acid monohydrate, preferably 5 to 500 mg, more preferably 10 to 300 mg and particularly preferably 20 to 200 mg based on a single dosage. The pharmaceutical composition according to the invention optionally comprises one or more filler which are for example selected from the group consisting of: microcrystalline cellulose, fiber cellulose, calcium phosphates and mannitol. Preferably according to the invention microcrystalline cellulose and mannitol is used. The pharmaceutical composition expediently comprises 20 to 80%, preferably 40 to 80%, particularly preferably 45 to 70% microcrystalline cellulose and 1 to 40%, preferably 5 to 30%, particularly preferably 10 to 20% mannitol. The pharmaceutical preparation according to the invention may comprise at least one disintegration auxiliary which is for example selected from the group consisting of starch, pre-gelatinized starch, starch glycolates, cross-linked polyvinylpyrrolidone, sodium carboxymethylcellulose (=croscarmellose sodium) and other salts of carboxymethylcellulose. A mixture of two disintegration agents can also be used. According to the invention the use of croscarmellose sodium is preferred. The pharmaceutical composition expediently comprises 3 to 35%, preferably 5 to 30% and particularly preferably 5 to 10% of the disintegration auxiliary(ies). The pharmaceutical preparation of the invention may comprise at least one lubricant selected from the group consisting of fatty acids and their salts. According to the invention the use of magnesium stearate is particularly preferred.

The pharmaceutical composition of the invention may comprise a flow agent which could be colloidas anhydrous silica or talcum powder. According to the invention the use of Colloidas anhydrous silica is particularly preferred. The flow agent is expediently used in an amount of 0.3 to 2.0%, particularly preferably from 0.4 to 1.5% and most preferably from 0.5 to 1%.

A particularly preferred pharmaceutical composition of the invention comprises:
5%-30% crystalline N-[5-(aminosulfonyl)-4-methyl-1,3-thiazol-2-yl]-N-methyl-2-[4-(2-pyridinyl)phenyl]acetamide methane-sulfonic acid monohydrate, 5%—10% croscarmellose-sodium, 0.5-0.7% magnesium stearate, 40%-70% micro-crystalline cellulose, 10%-20% mannitol and 0.5%-1% colloidal anhydrous silica.

The pharmaceutical compositions according to the invention can be administered to a patient in need thereof once daily at a once daily dose of about 20 to 750 mg of crystalline N-[5-(aminosulfonyl)-4-methyl-1,3-thiazol-2-yl]-N-methyl-2-[4-(2-pyridinyl)-phenyl]acetamide methanesulfonic acid monohydrate. The pharmaceutical compositions according to the invention can also be administered to a patient in need thereof thrice daily, twice daily, once daily, thrice weekly, twice weekly, or once weekly. The administration on a thrice weekly, twice weekly, or once weekly basis is preferred and especially preferred is a once weekly administration, i.e. an administration one time a week of a pharmaceutical composition containing between 400 mg to 600 mg of the inventive N-[5-(aminosulfonyl)-4-methyl-1,3-thiazol-2-yl]-N-methyl-2-[4-(2-pyridinyl)-phenyl]acetamide methanesulfonic acid monohydrate. Moreover it is preferred to start the administration of the mesylate monohydrate of the present invention with a high loading dose, for instance, with an initial single dose of 400 mg to 800 mg and to continue the administration with a lower dose of 100 mg to 150 mg per day or per week over the period of treatment.

Furthermore, the present invention also includes pharmaceutical compositions for the preferred parenteral application. Further ways of administration are dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application. The administered pharmaceutical compositions contain in addition to typical vehicles and/or diluents crystalline N-[5-(aminosulfonyl)-4-methyl-1,3-thiazol-2-yl]-N-methyl-2-[4-(2-pyridinyl)-phenyl]acetamide methanesulfonic acid monohydrate as active ingredient.

Further preferred are topical formulations of crystalline N-[5-(aminosulfonyl)-4-methyl-1,3-thiazol-2-yl]-N-methyl-2-[4-(2-pyridinyl)-phenyl]acetamide methane-sulfonic acid monohydrate for dermal or transdermal application. Preferred topical formulations are skin creams, skin lotions, emulsions, gels, suspensions, ointments, oils, lip sticks and balms.

The formulation may be added any conventional carriers, adjuvants and optionally other ingredients. Preferred auxiliaries originate from the group comprising or consisting of: preservatives, antioxidants, stabilizers, solubilizers and odors.

Ointments, pastes, creams and gels may include at least one conventional carriers, for example animal and vegetable fats, waxes, paraffins, starch, tragacanth, cellulose derivatives, polyethylene glycols, silicones, bentonites, silicic acid, talc and zinc oxide or mixtures of these substances. Solutions and emulsions may include conventional carriers such as solvents, solubilizing agents and emulsifiers, e.g. water, ethanol, isopropanol, ethyl carbonate, ethyl acetate, benzyl alcohol, benzyl benzoate, propylene glycol, 1,3-butyl glycol, oils, particularly cottonseed oil, peanut oil, corn oil, olive oil, castor oil and sesame oil, glycerol fatty acid esters, polyethylene glycols and fatty acid esters of sorbitan or mixtures of these substances. Suspensions may include conventional carriers such as liquid diluents, for example water, ethanol or propylene glycol, suspending agents, e.g. ethoxylated isostearyl alcohols, polyoxyethylene and polyoxyethylene sorbitan esters, microcrystalline cellulose, bentonite, agar-agar and tragacanth or mixtures of these substances.

An inventive composition may contain lipid particles in which crystalline N-[5-(aminosulfonyl)-4-methyl-1,3-thiazol-2-yl]-N-methyl-2-[4-(2-pyridinyl)-phenyl]acetamide methanesulfonic acid monohydrate is transported. The formulation of the pharmaceutical composition may also contain adjuvants, which are usually used in this type of composition, such as thickeners, emollients, humectants, surfactants, emulsifiers, preservatives, anti-foaming, perfumes, waxes, lanolin, propellants and dyes.

The inventive pharmaceutical composition may also be present as an alcoholic gel which comprises crystalline N-[5-(aminosulfonyl)-4-methyl-1,3-thiazol-2-yl]-N-methyl-2-[4-(2-pyridinyl)-phenyl]acetamide methanesulfonic acid monohydrate and one or more lower alcohols or lower polyols, such as ethanol, propylene glycol or glycerol, and a thickening agent, such as siliceous earth. The oily-alcoholic gels also comprise natural or synthetic oil or wax. Gels may also contain organic thickeners, such as Gum arabic, xanthan gum, sodium alginate, cellulose derivatives, preferably methylcellulose, hydroxymethylcellulose, hydroxyethyl-cellulose, hydroxypropylcellulose, hydroxypropylmethylcellulose or inorganic thickeners, such as aluminum silicates such as bentonite or a mixture of polyethylene glycol and polyethylene glycol stearate or distearate.

An inventive pharmaceutical composition may contain the following preservatives: phenoxyethanol, formaldehyde solution, parabens, pentanediol or sorbic acid.

As pharmaceutically acceptable carrier, excipient and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropyl methyl-cellulose, polyvinylpyrrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked micro-crystalline celluloses such as sodium croscarmellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Definition: As used herein, the term "1 vol." refers to 1 L per kg of the respective starting material (1 vol.=1 L per kg of the respective material or starting material).

Example 1

Synthesis of N-[5-(aminosulfonyl)-4-methyl-1,3-thiazol-2-yl]-N-methyl-2-[4-(2-pyridinyl)-phenyl] acetamide methanesulfonate monohydrate Step 1 (Suzuki-Miyaura Coupling and Saponification)

The inertized reactor is charged with bis(triphenylphosphine)palladium(II) chloride (0.010 eq.) and reinertized. Then, toluene (1.65 vol.) is added. After heating to 40° C., triethylamine (3.00 eq.) is added. A solution of ethyl-4-bromophenylacetate (1.00 eq.) in toluene (0.82 vol.) is added. The resulting suspension is heated to 90-95° C. prior to dosing pinacol borane (1.30 eq.) over a period of 60-90 min. Stirring at 90-95° C. is continued for at least 2 more h before conversion is checked by HPLC. After cooling to 10° C., 2-chloropyridine (1.00 eq.) is charged to the reaction mixture. Then, 30% NaOH (6.00 eq.) is added followed by heating to 55-60° C. Stirring at this temperature is continued for at least 4 h before conversion is checked by HPLC. Once conversion is deemed complete, the reaction mixture is concentrated at about 300 mbar until 0.8 vol. of distillate have been collected. The reaction mixture is diluted with water (2.72 vol.), cooled to 20° C. and the phases are separated. The organic layer is discarded, while the pH of the aqueous layer is adjusted to pH 1 by addition of 33% HCl at 20° C. MIBK (2.30 vol.) and Celite (165 g/kg) are added and the resulting mixture is stirred for at least 15 min at 20° C. before the solids are removed by filtration. The reactor and the filter cake are rinsed successively with water and the combined filtrate is transferred back into the reactor. The phases are separated and the aqueous layer is washed twice more with MIBK. After dilution with water, the aqueous acidic product solution was heated to 55° C. and filtered through a plug packed with Celite at the bottom and activated charcoal on top. The Celite/charcoal plug was washed once more with pre-heated water (0.5 vol., 55° C.) and the combined filtrate was charged back into the reactor. At 20° C., the pH was adjusted to ~3.0 by addition of 30% NaOH before the product solution was heated to 60° C. More NaOH was dosed to adjust the pH to 4.1-4.3. The resulting suspension was stirred for 1-1.5 h at 60° C. prior to being cooled to 20° C. After additional stirring for at least 1 h at this temperature, the product was filtered, washed twice with water, pre-dried in a flow of $N_2$ and finally dried in vacuo at 50-65° C. Typical yield: 38-42%.

Step 2 (Amide Coupling)

The reactor is charged with product from step 1 (1.00 eq.) and 4-methyl-2-(methylamino)-1,3-thiazole-5-sulfonamide (1.02 eq.). THF (7.08 vol.) and NMP (1.11 vol.) are added. The resulting suspension is cooled to 0° C. prior to adding 1-ethyl-3-(3-dimethyllaminopropyl)carbodiimide hydrochloride (1.23 eq.) in 4 equal portions over a period of >90 min. After at least 2 more h at 0° C., the reaction mixture is warmed to 20° C. At this temperature, stirring is continued for additional 2 h before conversion is checked by HPLC. Then, at 10-15° C. about 2% (0.2 vol.) of the reaction mixture are added to water (12.3 vol) within at least 5 min. The resulting thin suspension is stirred at 10-15° C. for at least 1 h prior to dosage of the remaining bulk of the reaction mixture over >4 h. Stirring at 10-15° C. is continued for at least 0.5 h before the solids are filtered off, washed with water and dried on a nutsche filter in a steady flow of $N_2$ until deemed sufficiently dry (LOD<45% w/w; LOD: Loss on drying).

The feed reactor is charged with the crude product, THF (8.15 vol.), and water (up to 1.17 vol. depending on LOD of crude product). The resulting suspension is heated to 60-65° C. and stirred for 1 h at this temperature. An almost clear solution is obtained which is subjected to polish filtration using a heatable lense filter heated to 60° C. The feed reactor, the transfer lines and the filter are successively rinsed with a mixture of THF (0.44 vol.) and purified water (0.06 vol.) at 60-65° C. The combined filtrate is collected in a separate reactor and heated to 50-55° C. To the reactor content, water (3.23 vol.) is dosed over at least 30 min. Stirring at 50-55° C. is continued for 1-1.5 h before another portion of water (8.93 vol.) is slowly added within 2 h. After stirring for 1-1.5 h at 50° C., the resulting suspension is cooled to 5° C. over 2.5 h and stirred for further 0.5 h. Then, the solids are filtered off, washed with water (3×2.96 vol.) and pre-dried on the nutsche filter in a steady flow of $N_2$. Final drying is accomplished in vacuo at 50-65° C. using a conical drier. Typical yield: 78-83%.

Step 3 (Salt Formation)

The reactor is charged with product from step 2 (1.00 eq.), ethanol (4.96 vol.) and water (4.96 vol.). After heating the resulting suspension to 50-55° C., methanesulfonic acid (1.15 eq.) is added within <15 min. Complete dissolution of starting materials is typically observed at the very end of addition. Immediately within the next 5 min, stirring is reduced to the minimum acceptable rate and the reaction mixture is seeded with N-[5-(aminosulfonyl)-4-methyl-1,3-thiazol-2-yl]-N-methyl-2-[4-(2-pyridinyl)-phenyl]acetamide methanesulfonate monohydrate (0.005 eq.) which was prepared in the desired polymorphic form in a preceding experiment. Slow stirring at 50-55° C. is continued for 60-90 min prior to cooling to 20-25° C. during >2.5 h. After stirring for 1 more h, the solids are filtered off, washed with ethanol/water 5:2 V/V (3.10 vol.), pre-dried in a nitrogen flow and transferred into a conical drier for final drying in vacuo at 20-60° C.

Typical yield: >95%.

Example 2

Tablet comprising 60 mg of N-[5-(aminosulfonyl)-4-methyl-1,3-thiazol-2-yl]-N-methyl-2-[4-(2-pyridinyl)-phenyl]acetamide (calculated as free base form) according to the invention as micronized active compound, content of active compound about 59% (based on an unvarnished tablet):

| | |
|---|---|
| crystalline N-[5-(aminosulfonyl)-4-methyl-1,3-thiazol-2-yl]-N-methyl-2-[4-(2-pyridinyl)-phenyl]acetamide methanesulfonic acid monohydrate, | 77.0 mg |
| Avicel PH 101 | 118.0 mg |
| Lactose, fine | 40.0 mg |
| Ac-Di-Sol | 20.0 mg |
| Polyinylpyrrolidone 25 | 10.0 mg |
| Magnesium stearate | 2.0 mg |

Example 3

Ointment comprising 30 mg of N-[5-(aminosulfonyl)-4-methyl-1,3-thiazol-2-yl]-N-methyl-2-[4-(2-pyridinyl)-phenyl]acetamide (calculated as free base form) according to the invention as micronized active compound

| | |
|---|---|
| crystalline N-[5-(aminosulfonyl)-4-methyl-1,3-thiazol-2-yl]-N-methyl-2-[4-(2-pyridinyl)-phenyl]acetamide methanesulfonic acid monohydrate, micronized | 38.4 mg |
| zinc oxide | 60.0 mg |
| talcum | 60.0 mg |
| glycerol | 120.0 mg |
| propyleneglycole | 40.0 mg |
| sterile water | 80.0 mg |

Example 4

Gel comprising 40 mg of N-[5-(aminosulfonyl)-4-methyl-1,3-thiazol-2-yl]-N-methyl-2-[4-(2-pyridinyl)-phenyl]acetamide (calculated as free base form) according to the invention as micronized active compound.

| | |
|---|---|
| crystalline N-[5-(aminosulfonyl)-4-methyl-1,3-thiazol-2-yl]-N-methyl-2-[4-(2-pyridinyl)-phenyl]acetamide methanesulfonic acid monohydrate, micronized | 51.2 mg |
| solution of sodium hydroxide | 30.0 mg |
| 1,2-propandiol | 80.0 mg |
| glycerol | 20.0 mg |
| polyacrylic acid | 60.0 mg |
| sterile water | 280.0 mg |

Example 5

Gel comprising 40 mg of N-[5-(aminosulfonyl)-4-methyl-1,3-thiazol-2-yl]-N-methyl-2-[4-(2-pyridinyl)-phenyl]acetamide (calculated as free base form) according to the invention as micronized active compound.

| | |
|---|---|
| crystalline N-[5-(aminosulfonyl)-4-methyl-1,3-thiazol-2-yl]-N-methyl-2-[4-(2-pyridinyl)-phenyl]acetamide methanesulfonic acid monohydrate, micronized | 51.2 mg |
| 1,2-propandiol | 80.0 mg |
| glycerol | 20.0 mg |
| polyacrylic acid | 60.0 mg |
| sterile water | 280.0 mg |

Example 6

Tablet comprising 50 mg of N-[5-(aminosulfonyl)-4-methyl-1,3-thiazol-2-yl]-N-methyl-2-[4-(2-pyridinyl)-phenyl]acetamide (calculated as free base form) according to the invention as micronized active compound, content of active compound about 59% (based on an unvarnished tablet):

| | |
|---|---|
| crystalline N-[5-(aminosulfonyl)-4-methyl-1,3-thiazol-2-yl]-N-methyl-2-[4-(2-pyridinyl)-phenyl]acetamide methanesulfonic acid monohydrate, micronized | 64.00 mg |
| Polyinylpyrrolidone 25 | 3.50 mg |
| Micro-crystalline cellulose | 20.00 mg |
| Croscamellose sodium | 10.00 mg |
| Magnesium stearate | 0.85 mg |
| optionally HPMC film coating | 3.00 mg |

Example 7

Crystal structure of N-[5-(aminosulfonyl)-4-methyl-1,3-thiazol-2-yl]-N-methyl-2-[4-(2-pyridinyl)phenyl]acetamide methanesulfonic acid monohydrate Formula $C_{19}H_{24}N_4O_7S_3$, M=516.62, F(000)=540, colorless plate, size 0.02·0.13·0.15 mm³, triclinic, space group P −1, Z=2, a=9.4908(7)Å, b=9.5545(7) Å, c=14.4137(9) Å, α=86.130(3)°, β=72.104(3)°, γ=68.253(4)°, V=1153.68(15) Å³, $D_{calc.}$=1.487 Mg m⁻³. The crystal was measured on a Nonius KappaCCD diffractometer at 293K using graphite-monochromated Mo $K_\alpha$-radiation with λ=0.71073 Å, $\Theta_{max}$=30.065°. Minimal/maximal transmission 0.95/0.99, μ=0.370 mm⁻¹. The COLLECT suite has been used for datacollection and integration. From a total of 43492 reflections, 6761 were independent (merging r=0.026). From these, 4955 were considered as observed (I>3.0σ(I)) and were used to refine 298 parameters. The structure was solved by direct methods using the program SIR92. Least-squares refinement against F was carried out on all non-hydrogen atoms using the program CRYSTALS. R=0.0313 (observed data), wR=0.0432 (all data), GOF=1.0736. Minimal/maximal residual electron density=−0.28/0.33 e Å$^3$. Chebychev polynomial weights were used to complete the refinement.

Single-crystal structure parameters for N-[5-(aminosulfonyl)-4-methyl-1,3-thiazol-2-yl]-N-methyl-2-[4-(2-pyridinyl)phenyl]acetamide methanesulfonic acid monohydrate are shown in FIG. 1A.

Characteristic peaks of batch BXR3NC1 obtained by X-ray powder diffraction analysis are shown in Table 3.

TABLE 3

Characteristic peaks of batch BXR3NC1 obtained by X-ray powder diffraction analysis (Cu K$_{alpha}$ irradiation).

| Angle (2-Theta °) | d value (Ångstrom) |
|---|---|
| 6.5 | 13.7 |
| 12.9 | 6.8 |
| 16.8 | 5.29 |
| 18.9 | 4.70 |
| 19.3 | 4.61 |
| 19.5 | 4.56 |
| 20.0 | 4.44 |
| 22.4 | 3.97 |
| 22.6 | 3.94 |
| 23.2 | 3.84 |
| 23.8 | 3.74 |
| 25.5 | 3.49 |
| 25.9 | 3.43 |
| 28.8 | 3.10 |
| 30.5 | 2.93 |
| 32.7 | 2.74 |
| 35.7 | 2.51 |

The 2-Theta values are rounded to 1 decimal place due to a normal deviation of +/−0.1°

Example 8

The exposure of rats to N-[5-(aminosulfonyl)-4-methyl-1,3-thiazol-2-yl]-N-methyl-2-[4-(2-pyridinyl)phenyl]acetamide in a repeated dose 13-week toxicity study performed with the free base N-[5-(aminosulfonyl)-4-methyl-1,3-thiazol-2-yl]-N-methyl-2-[4-(2-pyridinyl)phenyl]acetamide (free base) was compared to the exposures observed in a 26-week repeated dose toxicity study performed with the mesylate monohydrate. In both studies, the test items were administered as 0.5% (w/v) tylose suspensions, and the concentrations were adjusted to the equivalents of free base N-[5-(aminosulfonyl)-4-methyl-1,3-thiazol-2-yl]-N-methyl-2-[4-(2-pyridinyl)phenyl]acetamide.

Exposures were comparable after administration of 10, 50 and 250 mg/kg/day both after administration of the first dose (days 1, 2; Table 4), as well as after repeated dose administration for 13 weeks (Table 5). There was an indication of a possibly higher exposure after a dose of 10 mg/kg/day. Of note was the observation that exposures after administration of N-[5-(aminosulfonyl)-4-methyl-1,3-thiazol-2-yl]-N-methyl-2-[4-(2-pyridinyl)phenyl]acetamide mesylate monohydrate were higher, after doses of 50 and 250 mg/kg/day (adjusted to the equivalents of free base), as compared to exposures after administration of the free base. The extent of exposure increased by up to 2.7-fold for $C_{max}$ and 4-fold for AUC. It is concluded that N-[5-(aminosulfonyl)-4-methyl-1,3-thiazol-2-yl]-N-methyl-2-[4-(2-pyridinyl)phenyl]acetamide mesylate monohydrate gave rise to higher exposures as compared to those observed following administration of equimolecular doses (50 and 250 mg/kg/day) of free base equivalents of N-[5-(aminosulfonyl)-4-methyl-1,3-thiazol-2-yl]-N-methyl-2-[4-(2-pyridinyl)phenyl]acetamide. Such a major increase in the extent of exposure is thus indicative of the mesylate salts improved physicochemical properties giving rise to a more favourable dissolution profile with concomitant increase in systemic exposure relative to that observed following administration of the freebase.

This enhancement in exposure, following administration of the mesylate salt, therefore means that a higher exposure to the active ingredient is achieved giving rise to a greater efficacy and higher viral resistance barrier, both regarded as an essential feature for the treatment of viral infections. The enhancement of both efficacy and resistance barrier are judged to be prime features associated with the mesylate salt formulation

TABLE 4

Comparison of exposures in the 13-week toxicity (free base) and the 26-week toxicity (mesylate salt) studies in rats after one administration. M male, F female. $C_{max}$ is the maximal observed analyte concentration; $AUC_{(0-24)}$ is defined as the area under the analyte vs. time concentration up to 24 hours post dosing; calculated by linear up/ln down summation

| Dose | | Free base 13-week toxicity study (13-wts) day 1 | | Mesylate monohydrate 26-week toxicity study (26-wts) day 1 | | Exposure ratio 26-wts/13-wts. | |
|---|---|---|---|---|---|---|---|
| | | $C_{max}$ | $AUC_{(0-24)}$ | $C_{max}$ | $AUC_{(0-24)}$ | | |
| [mg/kg/day] | Gender | [ng/ml] | [ng × h/ml] | [ng/ml] | [ng × h/ml] | $C_{max}$ | $AUC_{(0-24)}$ |
| 10 | M | 13300 | 87900 | 16935 | 118752 | 1.3 | 1.4 |
| 50 | M | 30600 | 248000 | 70324 | 633522 | 2.3 | 2.6 |
| 250 | M | 53900 | 567000 | 133776 | 1982721 | 2.5 | 3.5 |
| 10 | F | 15300 | 159000 | 17237 | 175125 | 1.1 | 1.1 |
| 50 | F | 35300 | 409000 | 77824 | 912978 | 2.2 | 2.2 |
| 250 | F | 68900 | 966000 | 146142 | 2473155 | 2.1 | 2.6 |

TABLE 5

Comparison of exposures in the 13-week toxicity (free base) and the 26-week toxicity (mesylate monohydrate salt) studies in rats in week 13. M male, F female. $C_{max}$ is the maximal observed analyte concentration; $AUC_{(0-24)}$ is defined as the area under the analyte vs. time concentration up to 24 hours post dosing; calculated by linear up/ln down summation

| Dose | | Free base 13-week toxicity study (13-wts) week 13 | | Mesylate monohydrate 26-week toxicity study (26-wts) week 13 | | Exposure ratio 26-wts/13-wts | |
|---|---|---|---|---|---|---|---|
| [mg/kg/day] | Gender | $C_{max}$ [ng/ml] | $AUC_{(0-24)}$ [ng × h/ml] | $C_{max}$ [ng/ml] | $AUC_{(0-24)}$ [ng × h/ml] | $C_{max}$ | $AUC_{(0-24)}$ |
| 10 | M | 15000 | 133000 | 21840 | 227165 | 1.5 | 1.7 |
| 50 | M | 30000 | 332000 | 74719 | 959252 | 2.5 | 2.9 |
| 250 | M | 62800 | 661000 | 168968 | 2782092 | 2.7 | 4.2 |
| 10 | F | 25800 | 211000 | 25953 | 321135 | 1.0 | 1.5 |
| 50 | F | 40500 | 455000 | 106147 | 1205651 | 2.6 | 2.6 |
| 250 | F | 83000 | 1172000 | 217283 | 3584983 | 2.6 | 3.1 |

Figure 1C:
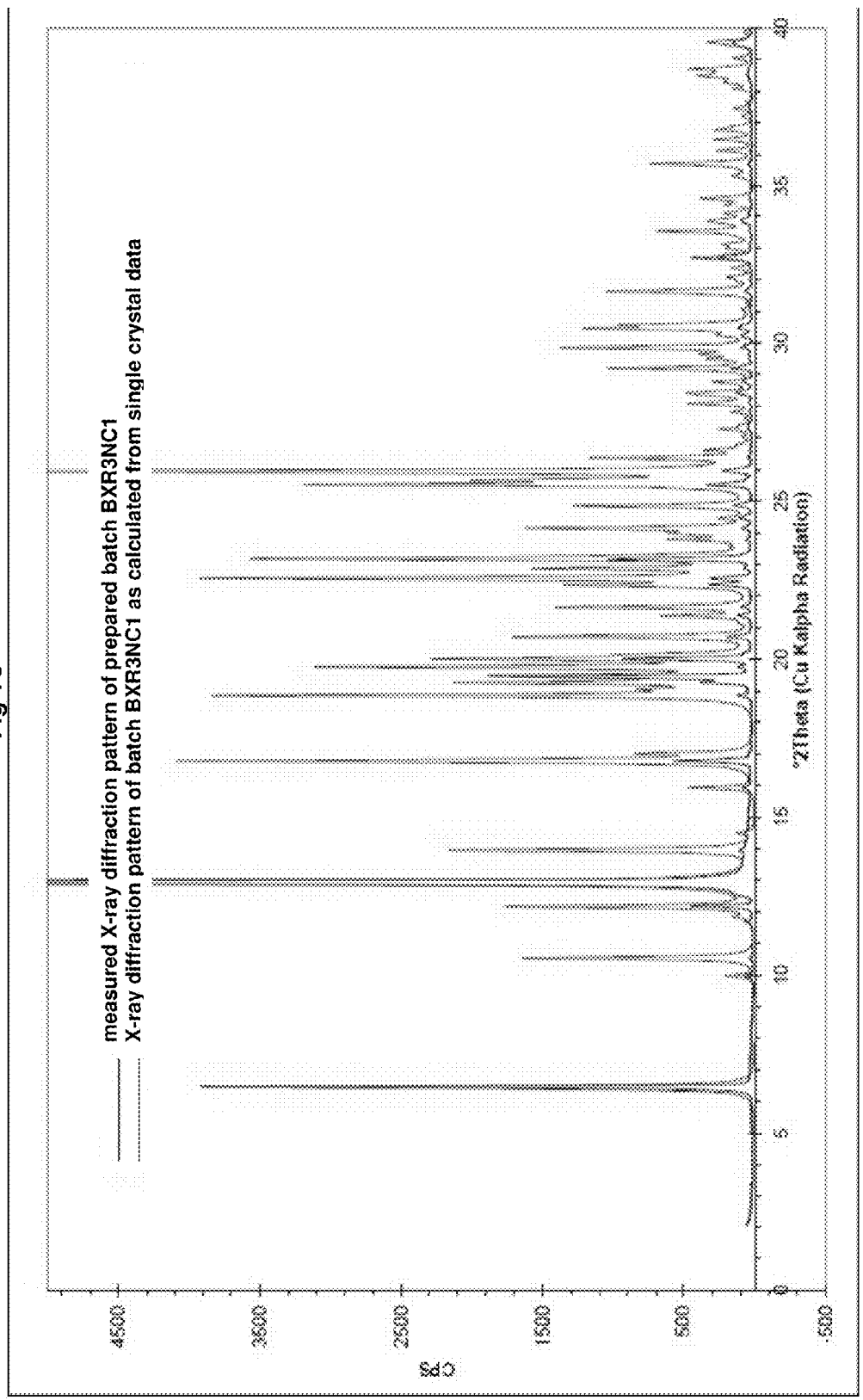
FIG. 1 shows
A) the single-crystal structure parameters for N-[5-(aminosulfonyl)-4-methyl-1,3-thiazol-2-yl]-N-methyl-2-[4-(2-pyridinyl)phenyl]acetamide methanesulfonic acid monohydrate (batch BXR3NC1),
B) the X-ray powder diffraction spectrum of N-[5-(aminosulfonyl)-4-methyl-1,3-thiazol-2-yl]-N-methyl-2-[4-(2-pyridinyl)phenyl]acetamide methanesulfonic acid monohydrate (batch BXR3NC1) as calculated from single crystal data, and
C) an overlay of the X-ray powder diffraction spectra of N-[5-(aminosulfonyl)-4-methyl-1,3-thiazol-2-yl]-N-methyl-2-[4-(2-pyridinyl)phenyl]acetamide methanesulfonic acid monohydrate of batch BXR3NC1 as measured (blue line) and as calculated (red line).
D) Measured X-ray powder pattern of batch BXR3NC1
Figure 1D:
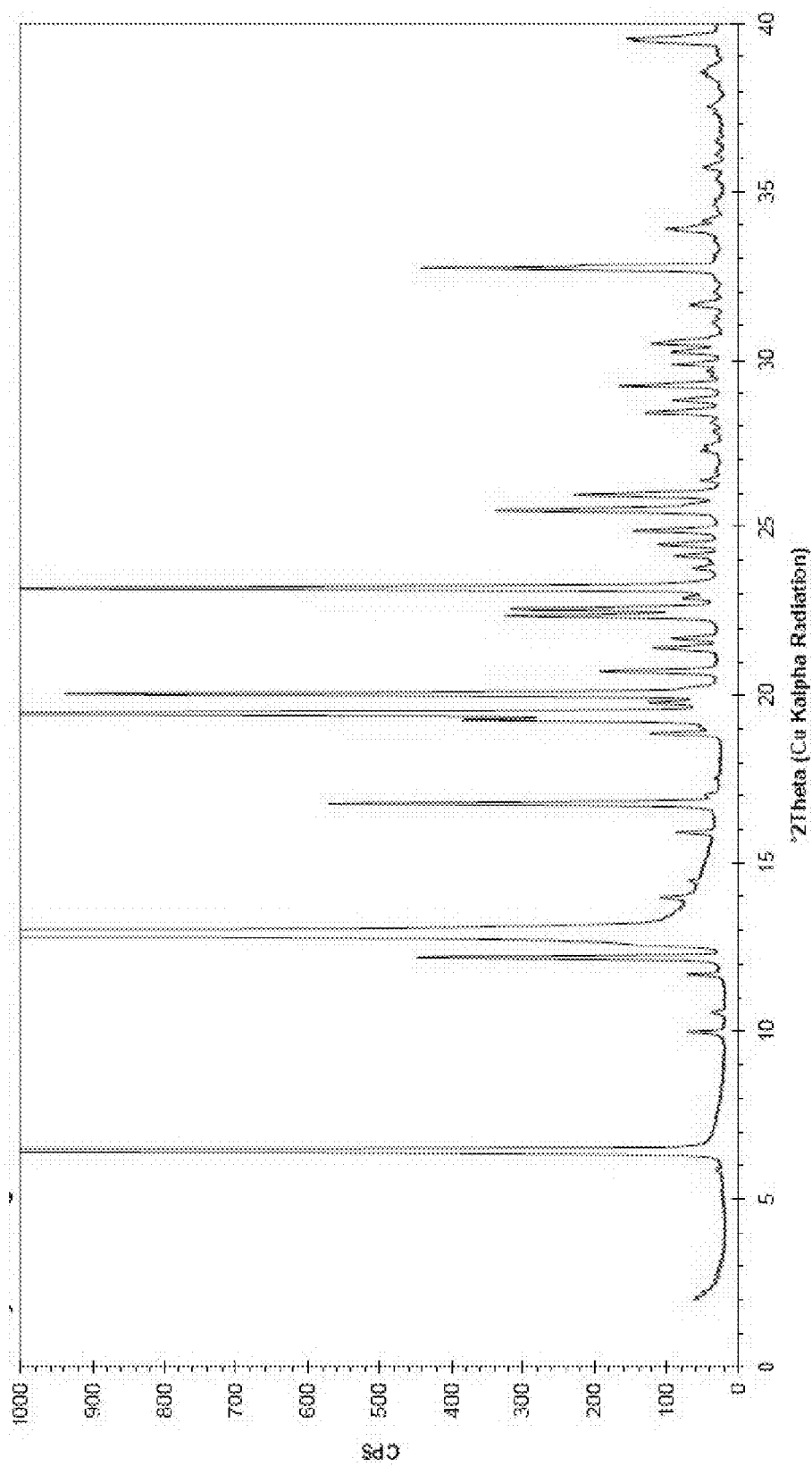
Figure 2:
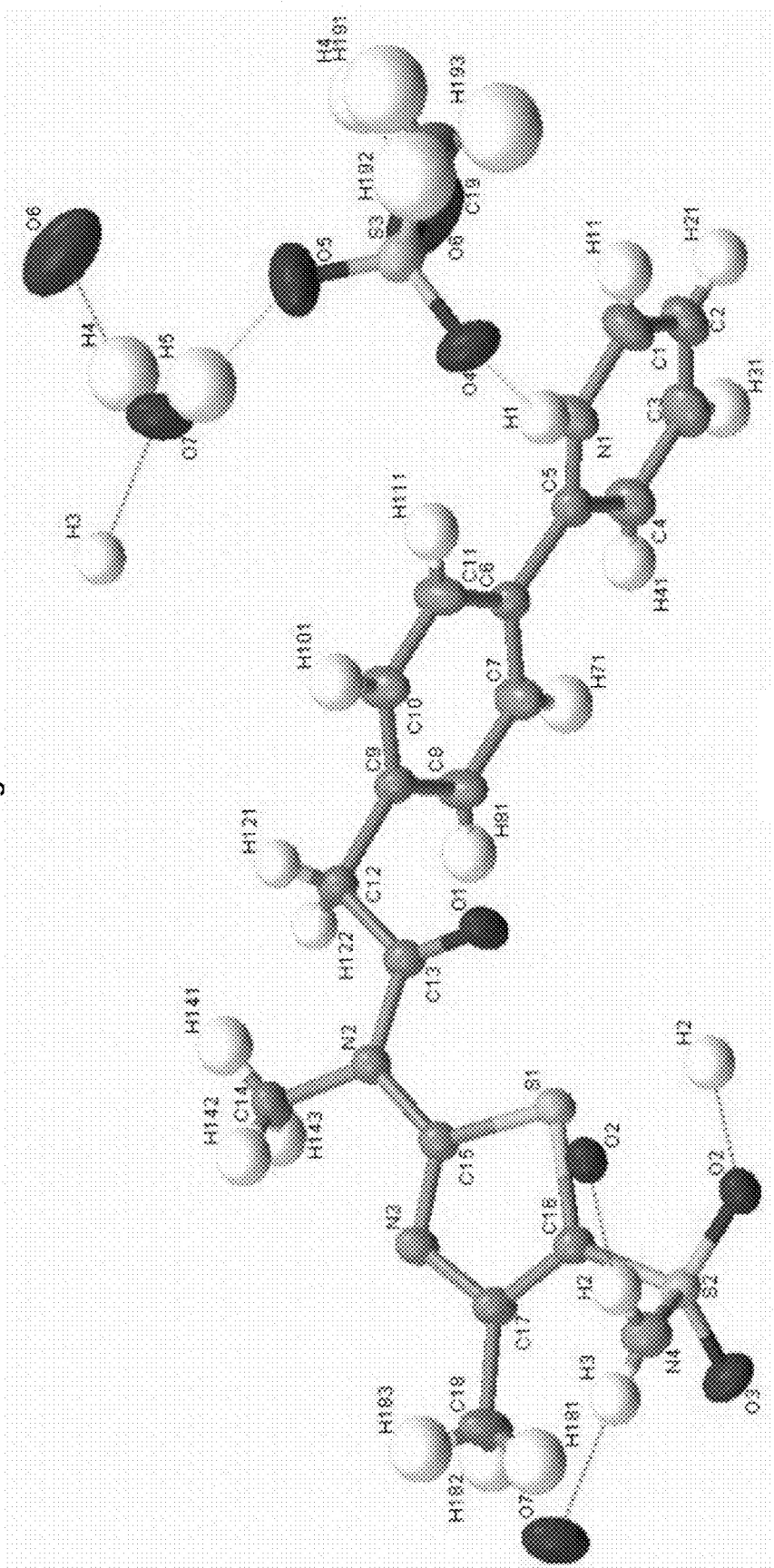
FIG. 2 shows the X-ray structure of the N-[5-(aminosulfonyl)-4-methyl-1,3-thiazol-2-yl]-N-methyl-2-[4-(2-pyridinyl)phenyl]acetamide methanesulfonic acid monohydrate with indicated hydrogen bridges. It is shown that the nitrogen atom of the pyridinyl ring (right side bottom) is protonated and that a hydrogen bridge is formed between the hydrogen, which protonates the pyridinyl ring nitrogen, and one oxygen of the mesylate anion, and that another hydrogen bridge is formed between another oxygen of the mesylate anion and the hydrogen of the water molecule while the other hydrogen of the water molecule forms a hydrogen bridge with the oxygen of another mesylate anion.
Figure 3:
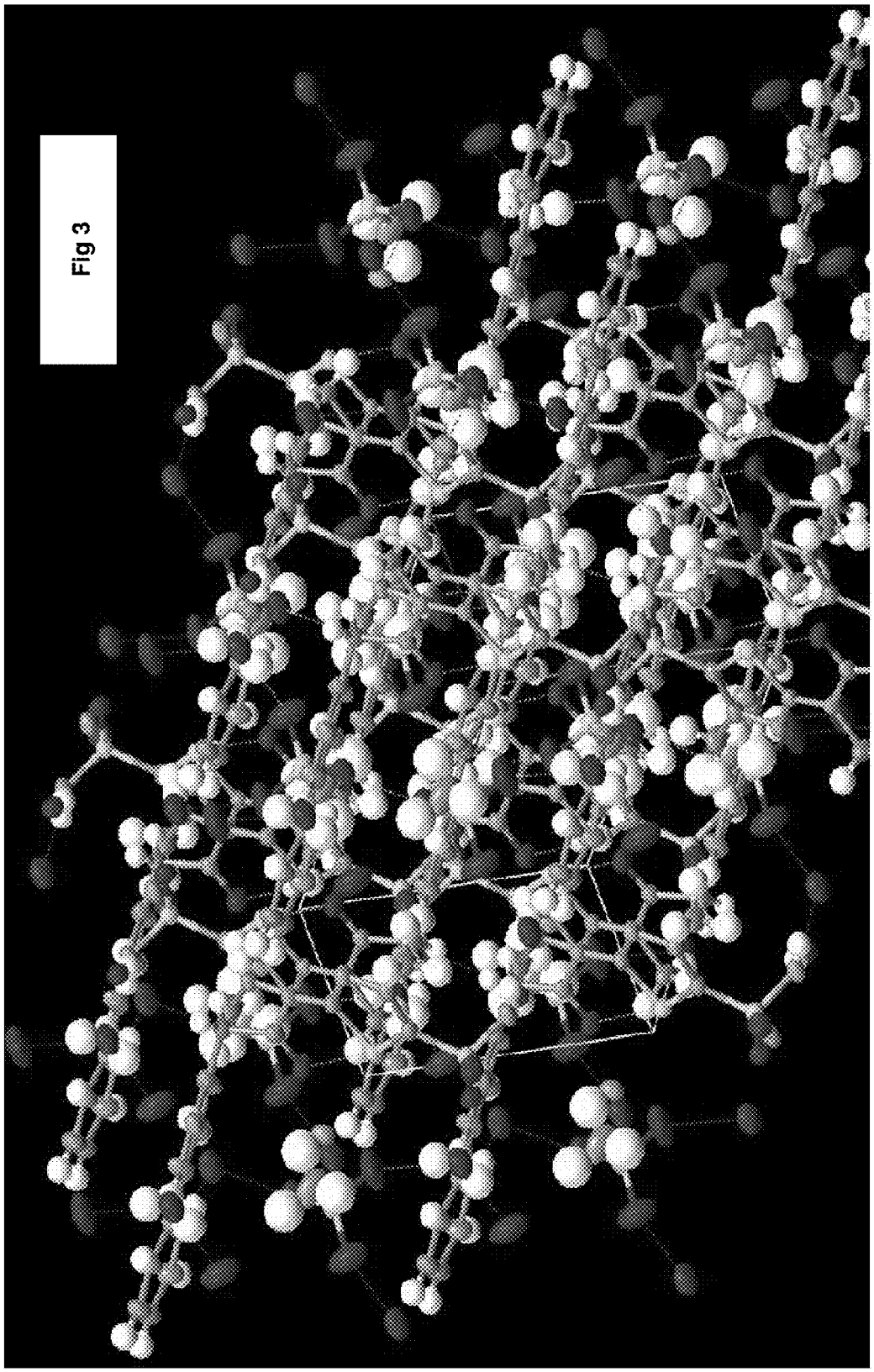
FIG. 3 shows the single-crystal X-ray structure analysis of the N-[5-(amino-sulfonyl)-4-methyl-1,3-thiazol-2-yl]-N-methyl-2-[4-(2-pyridinyl)phenyl]acetamide methanesulfonic acid monohydrate as packing within the crystal. It is shown that the phenylpyridinyl ring systems are oriented in planes, which are parallel to each other.

The invention claimed is:
1. A crystalline N-[5-(aminosulfonyl)-4-methyl-1,3-thiazol-2-yl]-N-methyl-2-[4-(2-pyridinyl)-phenyl]acetamide methanesulfonic acid monohydrate having a purity above 96 weight-%.
2. A process for preparing the crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 1, comprising step A:
reacting a compound of formula A*

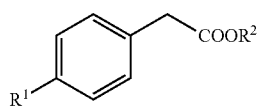

A* wherein
$R^1$ represents a leaving group and
$R^2$ represents an alkyl residue with 1 to 6 carbon atoms or a cycloalkyl residue with 3 to 6 carbon atoms
with a boronic acid compound, borolane, borinane or diboronic acid reagent under elimination of $R^1$—H or $R^1$—B$(OR)_2$ and formation of an intermediate boronic acid compound of compound A,
wherein the intermediate boronic acid compound is then reacted with a pyridine compound of formula B*

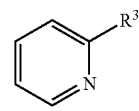

B* wherein
$R^3$ represents a leaving group
under basic conditions in order to directly obtain (4-pyridin-2-ylphenyl)acetic acid which is then purified
step B:
reacting the obtained (4-pyridin-2-ylphenyl)acetic acid with 4-methyl-2-(methylamino)-1,3-thiazole-5-sulfonamide

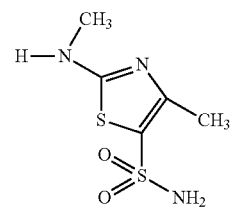

to obtain N-[5-(aminosulfonyl)-4-methyl-1,3-thiazol-2-yl]-N-methyl-2-[4-(2-pyridinyl)phenyl]acetamide of the following formula

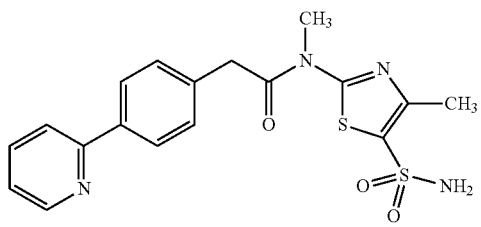 [SMILES: Cc1nc(N(C)C(=O)Cc2ccc(-c3ccccn3)cc2)sc1S(N)(=O)=O]

and
step C:
converting the N-[5-(aminosulfonyl)-4-methyl-1,3-thiazol-2-yl]-N-methyl-2-[4-(2-pyridinyl)phenyl]acetamide with methanesulfonic acid in a mixture of an organic solvent and water to crystalline N-[5-(aminosulfonyl)-4-methyl-1,3-thiazol-2-yl]-N-methyl-2-[4-(2-pyridinyl)phenyl]acetamide methanesulfonic acid monohydrate of the following formula

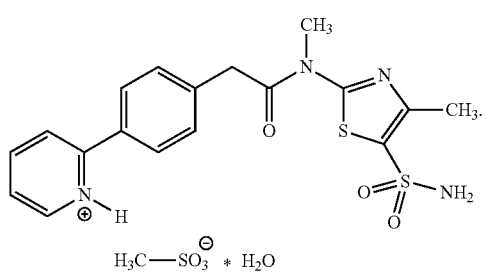

3. The process according to claim 2, wherein $R^1$ and $R^3$ are independently of each other selected from the group consisting of —F, —Cl, —Br, —I, —OMs, —OTf and —OTs.

4. The process according to claim 2, wherein the boronic acid compound, borolane, borinane or diboronic acid reagent is one of the following:

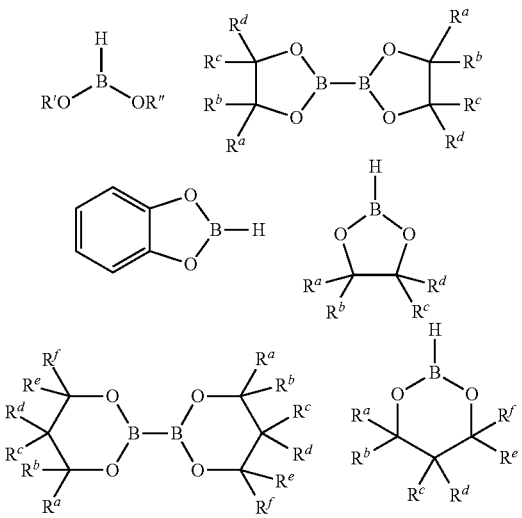

wherein
R', R", $R^a$, $R^b$, $R^c$, $R^d$, $R^e$ and $R^f$ represent independently of each other a substituted or unsubstituted, linear or branched alkyl group with 1 to 10 carbon atoms or cycloalkyl group with 3 to 10 carbon atoms.

5. The process according to claim 2, wherein for the preparation of the intermediate boronic acid compound or borolane reagent, the reagents palladium acetate, triethylamine and triphenylphosphine or $PdCl_2(PPh_3)_2$ and triethylamine are used.

6. The process according to claim 2, wherein Step B is carried out with EDC×HCl as coupling agent in a THF/NMP solvent mixture.

7. The process according to claim 2, wherein the mixture of N-[5-(aminosulfonyl)-4-methyl-1,3-thiazol-2-yl]-N-methyl-2-[4-(2-pyridinyl)phenyl]acetamide in an organic solvent and water yields a supersaturated solution upon addition of methanesulfonic acid at an elevated temperature from which the N-[5-(aminosulfonyl)-4-methyl-1,3-thiazol-2-yl]-N-methyl-2-[4-(2-pyridinyl)phenyl]-acetamide methanesulfonic acid monohydrate crystallizes after either extended stirring, seeding or cooling.

8. The process according to claim 2 further comprising step D:
preparing a pharmaceutical composition of the crystalline N-[5-(aminosulfonyl)-4-methyl-1,3-thiazol-2-yl]-N-methyl-2-[4-(2-pyridinyl)phenyl]-acetamide methanesulfonic acid monohydrate with at least one pharmaceutically acceptable carrier, excipient, solvent and/or diluent.

9. A crystalline N-[5-(aminosulfonyl)-4-methyl-1,3-thiazol-2-yl]-N-methyl-2-[4-(2-pyridinyl)-phenyl]acetamide methanesulfonic acid monohydrate, wherein one or more of the following conditions 1, 2, 3 and/or 4 is satisfied:
condition 1:
the crystalline N-[5-(aminosulfonyl)-4-methyl-1,3-thiazol-2-yl]-N-methyl-2-[4-(2-pyridinyl)-phenyl]acetamide methanesulfonic acid monohydrate is a polymorph of crystalline N-[5-(aminosulfonyl)-4-methyl-1,3-thiazol-2-yl]-N-methyl-2-[4-(2-pyridinyl)-phenyl]acetamide methanesulfonic acid monohydrate, wherein the X-Ray diffraction pattern of the polymorph comprises 2-Theta angle values of 6.5, 12.9, 16.8, 18.9, 19.3, 19.5, 20.0, 22.4, 22.5, 23.2, 23.8, 25.5, 25.9, 28.8, 30.5, 32.7, and 35.7 degrees;
condition 2:
the crystalline N-[5-(aminosulfonyl)-4-methyl-1,3-thiazol-2-yl]-N-methyl-2-[4-(2-pyridinyl)-phenyl]acetamide methanesulfonic acid monohydrate exhibits a polymorphic form described as follows:

| | |
|---|---|
| F(000) | 540 |
| description and size of crystal | colorless plate, 0.02 · 0.13 · 0.15 mm3 |
| absorption coefficient | 0.370 mm−1 |
| min/max transmission | 0.95/0.99 |
| temperature | 293K |
| radiation(wavelength) | Mo Ka($\lambda$ = 0.71073 Å) |
| Crystal system, space group | triclinic, P−1 |
| a | 9.4908(7) Å |
| b | 9.5545(7) Å |
| c | 14.4137(9) Å |
| $\alpha$ | 86.130(3)° |
| $\beta$ | 72.104(3)° |
| $\gamma$ | 68.253(4)° |
| V | 1153.68(15) Å3 |
| min/max (−) | 2.426° / 30.065° |
| # of collected reflections | 43492 |
| # of independent reflections | 6761 (merging r = 0.026) |
| # of observed reflections | 4955 (1 > 3.0$\sigma$(I)) |

| | |
|---|---|
| # of refined parameters | 298 |
| r | 0.0313 (observed data with ) |
| rW | 0.0432 (all data) |
| goodness of fit | 1.0736 |
| residual electron density | −0.28/0.33 e Å3; | condition 3:

The crystalline N-[5-(aminosulfonyl)-4-methyl-1,3-thiazol-2-yl]-N-methyl-2-[4-(2-pyridinyl)-phenyl]acetamide methanesulfonic acid monohydrate is in combination with acetylsalicylic acid, trifluridine, idoxuridine, foscarnet, cidofovir, ganciclovir, aciclovir, penciclovir, valaciclovir and/or famciclovir;

condition 4:

the crystalline N-[5-(aminosulfonyl)-4-methyl-1,3-thiazol-2-yl]-N-methyl-2-[4-(2-pyridinyl)-phenyl]acetamide methanesulfonic acid monohydrate is a polymorph of crystalline N-[5-(aminosulfonyl)-4-methyl-1,3-thiazol-2-yl]-N-methyl-2-[4-(2-pyridinyl)-phenyl]acetamide methanesulfonic acid monohydrate, wherein the X-Ray diffraction pattern of the polymorph comprises 2-Theta angle values of 6.5, 12.9, 16.8, 20.0 and 23.8 degrees.

10. The crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 9, wherein the crystalline N-[5-(aminosulfonyl)-4-methyl-1,3-thiazol-2-yl]-N-methyl-2-[4-(2-pyridinyl)-phenyl]acetamide methanesulfonic acid monohydrate is a polymorph of crystalline N-[5-(aminosulfonyl)-4-methyl-1,3-thiazol-2-yl]-N-methyl-2-[4-(2-pyridinyl)-phenyl]acetamide methanesulfonic acid monohydrate, wherein the X-Ray diffraction pattern of the polymorph comprises 2-Theta angle values of 6.5, 12.9, 16.8, 18.9, 19.3, 19.5, 20.0, 22.4, 22.5, 23.2, 23.8, 25.5, 25.9, 28.8, 30.5, 32.7, and 35.7 degrees.

11. The crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 8, which exhibits a polymorphic form described as follows:

| | |
|---|---|
| F(000) | 540 |
| description and size of crystal | colorless plate, 0.02 · 0.13 · 0.15 mm3 |
| absorption coefficient | 0.370 mm−1 |
| min/max transmission | 0.95/0.99 |
| temperature | 293K |
| radiation(wavelength) | Mo Kα(λ = 0.71073 Å) |
| Crystal system, space group | triclinic, P−1 |
| a | 9.4908(7) Å |
| b | 9.5545(7) Å |
| c | 14.4137(9) Å |
| α | 86.130(3)° |
| β | 72.104(3)° |
| γ | 68.253(4)° |
| V | 1153.68(15) Å3 |
| min/max (−) | 2.426° / 30.065° |
| # of collected reflections | 43492 |
| # of independent reflections | 6761 (merging r = 0.026) |
| # of observed reflections | 4955 (1 > 3.0σ(I)) |
| # of refined parameters | 298 |
| r | 0.0313 (observed data with ) |
| rW | 0.0432 (all data) |
| goodness of fit | 1.0736 |
| residual electron density | −0.28/0.33 e Å3. |

12. The crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 8 in combination with acetylsalicylic acid, trifluridine, idoxuridine, foscarnet, cidofovir, ganciclovir, aciclovir, penciclovir, valaciclovir and/or famciclovir.

13. A method for the treatment or prophylaxis of a herpes simplex virus infection or for the prevention of transmission of a herpes simplex virus infection, comprising administering to a subject in need thereof an effective amount of the crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 9.

14. The method according to claim 13, which is for the treatment of a herpes simplex virus infection.

15. A pharmaceutical composition containing crystalline N-[5-(aminosulfonyl)-4-methyl-1,3-thiazol-2-yl]-N-methyl-2-[4-(2-pyridinyl)phenyl]acetamide methane-sulfonic acid monohydrate according to claim 9 together with at least one pharmaceutically acceptable carrier, excipient, solvent and/or diluent.

16. The crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 9, wherein the crystalline N-[5-(aminosulfonyl)-4-methyl-1,3-thiazol-2-yl]-N-methyl-2-[4-(2-pyridinyl)-phenyl]acetamide methanesulfonic acid monohydrate is a polymorph of crystalline N-[5-(aminosulfonyl)-4-methyl-1,3-thiazol-2-yl]-N-methyl-2-[4-(2-pyridinyl)-phenyl]acetamide methanesulfonic acid monohydrate, wherein characterised in that the X-Ray diffraction pattern of the polymorph comprises 2-Theta angle values of 6.5, 12.9, 16.8, 20.0 and 23.8 degrees.

17. The crystalline N-[5-(aminosulfonyl)-4-methyl-1,3-thiazol-2-yl]-N-methyl-2-[4-(2-pyridinyl)-phenyl]acetamide methanesulfonic acid monohydrate of claim 1 having a purity above 98 weight-%.

18. The crystalline N-[5-(aminosulfonyl)-4-methyl-1,3-thiazol-2-yl]-N-methyl-2-[4-(2-pyridinyl)-phenyl]acetamide methanesulfonic acid monohydrate of claim 1 having a purity above 99 weight-%.

19. The crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 15 in combination with acetylsalicylic acid, trifluridine, idoxuridine, foscarnet, cidofovir, ganciclovir, aciclovir, penciclovir, valaciclovir and/or famciclovir.

20. A method for the treatment or prophylaxis of a herpes simplex virus infection or for the prevention of transmission of a herpes simplex virus infection, comprising administering to a subject in need thereof an effective amount of the crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 1.

21. The method according to claim 20, which is for the treatment of a herpes simplex virus infection.

22. A pharmaceutical composition containing crystalline N-[5-(aminosulfonyl)-4-methyl-1,3-thiazol-2-yl]-N-methyl-2-[4-(2-pyridinyl)phenyl]acetamide methane-sulfonic acid monohydrate according to claim 1 together with at least one pharmaceutically acceptable carrier, excipient, solvent and/or diluent.

23. The method according to claim 13, which is for the prevention of transmission of a herpes simplex virus infection.

24. The method according to claim 20, which is for the prevention of transmission of a herpes simplex virus infection.

25. A process for preparing the crystalline N-[5-(aminosulfonyl)-4-methyl-1,3-thiazol-2-yl]-N-methyl-2-[4-(2-pyridinyl)-phenyl]acetamide methanesulfonic acid monohydrate according to claim 9, comprising step A:
reacting a compound of formula A*

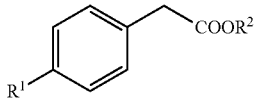

wherein
R¹ represents a leaving group and
R² represents an alkyl residue with 1 to 6 carbon atoms or a cycloalkyl residue with 3 to 6 carbon atoms
with a boronic acid compound, borolane, borinane or diboronic acid reagent under elimination of R¹—H or R¹—B(OR)₂ and formation of an intermediate boronic acid compound of compound A,
wherein the intermediate boronic acid compound is then reacted with a pyridine compound of formula B*

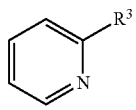

wherein
R³ represents a leaving group
under basic conditions in order to directly obtain (4-pyridin-2-ylphenyl)acetic acid which is then purified
step B:
reacting the obtained (4-pyridin-2-ylphenyl)acetic acid with 4-methyl-2-(methylamino)-1,3-thiazole-5-sulfonamide

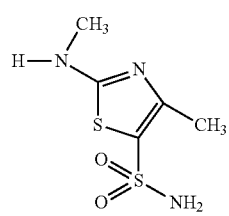

to obtain N-[5-(aminosulfonyl)-4-methyl-1,3-thiazol-2-yl]-N-methyl-2-[4-(2-pyridinyl)phenyl]acetamide of the following formula

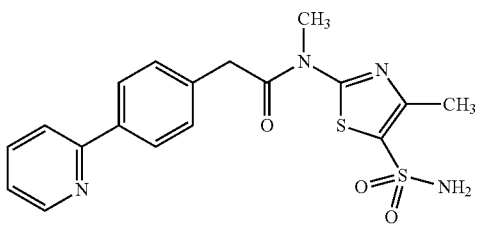 [SMILES: Cc1nc(N(C)C(=O)Cc2ccc(-c3ccccn3)cc2)sc1S(N)(=O)=O]

and
step C:
converting the N-[5-(aminosulfonyl)-4-methyl-1,3-thiazol-2-yl]-N-methyl-2-[4-(2-pyridinyl)phenyl]acetamide with methanesulfonic acid in a mixture of an organic solvent and water to crystalline N-[5-(aminosulfonyl)-4-methyl-1,3-thiazol-2-yl]-N-methyl-2-[4-(2-pyridinyl)phenyl]acetamide methanesulfonic acid monohydrate of the following formula

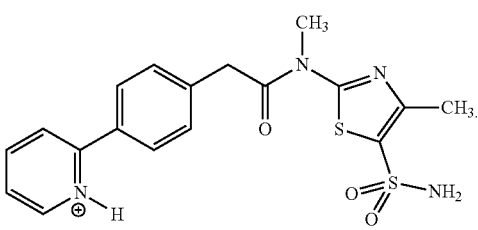

* * * * *

UNITED STATES PATENT AND TRADEMARK OFFICE
CERTIFICATE OF CORRECTION

PATENT NO. : 9,340,535 B2  
APPLICATION NO. : 14/347287  
DATED : May 17, 2016  
INVENTOR(S) : Wilfried Schwab et al.

Page 1 of 1

It is certified that error appears in the above-identified patent and that said Letters Patent is hereby corrected as shown below:

On the Title Page

In Item (72), change --Vogtli-- to --Vögtli--.

Signed and Sealed this  
Eighth Day of July, 2025

Coke Morgan Stewart  
*Acting Director of the United States Patent and Trademark Office*